(12) United States Patent
Cosson et al.

(10) Patent No.: US 7,863,413 B2
(45) Date of Patent: Jan. 4, 2011

(54) PEPTIDE PROTEIN TRANSLATION INHIBITOR AND THE USE THEREOF FOR PROTEIN TRANSLATION CONTROL

(75) Inventors: Bertrand Cosson, Le Crouais (FR); Luc Paillard, Montreuil le Gast (FR); Vincent Legagneux, Rennes (FR); Howard Osborne, Saint Senoux (FR)

(73) Assignees: Centre National de la Recherche Scientifique (CNRS), Paris (FR); Universite de Rennes 1, Rennes (FR)

( * ) Notice: Subject to any disclaimer, the term of this patent is extended or adjusted under 35 U.S.C. 154(b) by 968 days.

(21) Appl. No.: 10/565,438

(22) PCT Filed: Jul. 20, 2004

(86) PCT No.: PCT/FR2004/050345

§ 371 (c)(1),
(2), (4) Date: Jan. 20, 2006

(87) PCT Pub. No.: WO2005/010038

PCT Pub. Date: Feb. 3, 2005

(65) Prior Publication Data

US 2007/0105764 A1 May 10, 2007

(30) Foreign Application Priority Data

Jul. 21, 2003 (FR) .................................. 03 50357

(51) Int. Cl.
*A61K 38/00* (2006.01)
*A61K 51/00* (2006.01)

(52) U.S. Cl. .......................... 530/324; 514/2; 424/1.69

(58) Field of Classification Search ....................... None
See application file for complete search history.

(56) References Cited

U.S. PATENT DOCUMENTS

2003/0194704 A1* 10/2003 Penn et al. .................... 435/6
2007/0083334 A1* 4/2007 Mintz et al. .................. 702/19

OTHER PUBLICATIONS

Paillard, Luc et al.: "East of EDEN was a poly(A) tail", Biology of the Cell, vol. 95, No. 3-4, 2003, pp. 211-219, XP-002262151.
Minshall, Nicola et al.: "A conserved role of a DEAD box helicase in mRNA masking", RNA, vol. 7, No. 12, 2001, pp. 1728-1742, XP-001156011.
Coller, Jeffery et al.: "Tethered function assays using 3' untranslated regions", Methods, vol. 26, No. 2, 2002, pp. 142-150, XP-002262153.
Takahashi, Nobuhiro et al.: "Coexpression of the CUG-Binding Protein Reduces DM Protein Kinase Expression in COS Cells", Journal of Biochemistry, vol. 130, No. 5, 2001, pp. 581-587, XP-002262154.
Good, Peter et al.: "A Family of Human RNA-binding Proteins Related to the *Drosophila* Bruno Translational Regulator", Journal of Biological Chemistry, vol. 275, No. 37, Sep. 2000, pp. 28583-28592, XP-002262155.
Castagnetti, Stefania et al.: "Control of *oskar* mRNA translation by Bruno in a novel cell-free system from *Drosophila* ovaries", Development, vol. 127, No. 5, Mar. 2000, pp. 1063-1068, XP-002262156.

* cited by examiner

*Primary Examiner*—Maury Audet
(74) *Attorney, Agent, or Firm*—Young & Thompson

(57) ABSTRACT

A peptide protein translation inhibitor has a size greater than 250 amino acids and it includes an amino acid sequence which is at least for 85% identical to an amino acid sequence SEQ ID No 1. It also relates to a fusion polypeptide which specifically inhibits an interesting target polynucleotide translation, in which the polypeptide includes the above defined inhibiting peptide fused with a RNA binding protein.

4 Claims, 7 Drawing Sheets

US 7,863,413 B2

PEPTIDE PROTEIN TRANSLATION INHIBITOR AND THE USE THEREOF FOR PROTEIN TRANSLATION CONTROL

FIELD OF THE INVENTION

The present invention relates to the field of the regulation of protein synthesis by control of the post-transcriptional steps of translation of the messenger RNAs into proteins. The principal industrial applications of the invention are the control of the production of proteins of interest in a bioreactor, the control of the production of proteins of interest in cellular therapy (somatic gene therapy), or also the control of the production of viral proteins in the context of antiviral therapies.

PRIOR ART

In general, there is a need in the state of the art to dispose of systems of control of the production of target proteins of interest, in particular in the field of the production of proteins in a bioreactor as well as in various types of medical therapies.

In certain cases, a general inhibition of the synthesis of the proteins produced by certain cells whose elimination is desired, like for example tumour cells, is required.

In other cases, an attempt is made to stimulate or, on the contrary, to inhibit the production of only one or several predetermined target proteins, like for example proteins of therapeutic interest, whose controlled expression is desired at well-defined times, for example in the production processes of proteins of interest by cells cultivated in bioreactors or also by cells used in somatic cellular gene therapy.

Proteins capable of acting at the post-transcriptional level on the level of translation of proteins by cells are known in the state of the art. The post-transcriptional biological activity of certain proteins may consist in a modification of the metabolism of the messenger RNAs, for example in a modification of the stability and half-life of the messenger RNAs, by an activation of the translation of the messenger RNAs or also by a modification of the transport or localisation of the messenger RNAs.

Thus, it has been shown that proteins derived from yeast, such as Pab1p, Pub1p, She2p, She3p; derived from *Xenopus* such as Xp54 and PAP1; or also mammalian proteins such as hUPF1, hUPF2, hUPF3a, hUPF3b, RNP S1, Y14, DEK, REF2, SRm160, eIF4E, eIF4G, REV, TAP1 and NXF3 were capable, after specific binding to the messenger RNA, of modifying the metabolism of the messenger RNA to which these proteins are bound, for example by stabilising this messenger RNA, by stimulating the translation of the messenger RNA, by stimulating the nucleus-cytoplasm export of the messenger RNA or by stimulating the polyadenylation of the messenger RNA (COLLER et al., 2002).

In order to test the biological activity of the different proteins capable of acting on the various post-transcriptional steps of the expression of the genes, i.e. on the different aspects of the metabolism of the messenger RNAs mentioned above, it has been suggested, in the state of the art, that the protein whose function is tested be fused with an RNA binding protein of known specificity, such as the protein MS2CP. The activity of the fusion protein (test protein-RNA binding protein) is tested on a DNA reporter construction coding for a messenger RNA comprising (i) the target nucleotide motif of the RNA binding protein and (ii) an open reading frame encoding a reporter protein, like luciferase or beta-globin (COLLER et al., 2002, PCT application N° WO 99/60.408).

The use has also been suggested of a fusion polypeptide comprising an RNA binding protein fused with a protein derived from the factor eIF4G in order to specifically activate the translation of proteins of interest (PCT application N° WO 00/53.779).

The protein EDEN-BP from *Xenopus laevis* was the first trans-acting factor for which an essential role in the specificity of de-adenylation of the messenger RNAs was demonstrated directly (PAILLARD et al., 1998). Subsequently, it was shown that the protein CUG-BP, which is encoded in the orthologous human gene of the gene coding for EDEN-BP, is probably a factor with a de-adenylation function responsible for the post-transcriptional control of the messenger RNA of the proto-oncogene c-Jun in mammalian cells (PAILLARD et al., 2002).

There is a need in the state of the art for constructions coding for a protein capable of acting on the messenger RNA in order to inhibit the translation of proteins in general or also to inhibit the translation of pre-defined target proteins.

SUMMARY OF THE INVENTION

A peptide inhibitor of protein translation is provided according to the invention, characterised in that its length is up to 250 amino acids and in that it comprises an amino acid sequence possessing at least 85 percent identity with the amino acid sequence SEQ ID No 1.

Another subject of the invention consists of a fusion polypeptide capable of specifically inhibiting the translation of a target polynucleotide of interest, characterised in that said polypeptide comprises a peptide inhibitor such as defined above, said peptide inhibitor being fused with an RNA binding protein.

The invention also provides nucleic acids comprising a polynucleotide coding for the peptide inhibitor or also the fusion polypeptide defined above.

The invention relates to a system of control of the translation of a polynucleotide of interest comprising:
 (a) a first nucleic acid consisting of a nucleic acid coding for a fusion peptide such as defined above;
 (b) a second nucleic acid comprising:
  (i) at least one copy of a target nucleotide sequence of the RNA binding protein contained in the fusion polypeptide encoded in the first nucleic acid such as defined in (a);
  (ii) the polynucleotide of interest.

The invention also relates to vectors in which are inserted the various nucleic acids included in the system of control of the translation of a polynucleotide of interest defined above, as well as to processes for the in vitro control of the translation of a target polynucleotide of interest, said processes making use of the translation control system defined above.

The invention also relates to kits designed for the control of the translation of a target polynucleotide of interest.

The invention also relates to the use of a control system or kit such as defined above for the control of the translation of a target polynucleotide of interest.

The invention also relates to pharmaceutical compositions comprising a fusion polypeptide including a peptide inhibitor of protein translation, said peptide being fused with an RNA binding protein, as described above.

The vector also includes a gene for resistance to neomycin ("Neo'") placed under the control of the promoter of the SV40 virus.

The vector also includes an open reading frame coding for a protein for resistance to ampicillin.

The 3' end of the open reading frame coding for the fusion polypeptide includes a polyadenylation signal sequence derived from the cDNA coding for the bovine growth hormone BGH.

Figure 3:
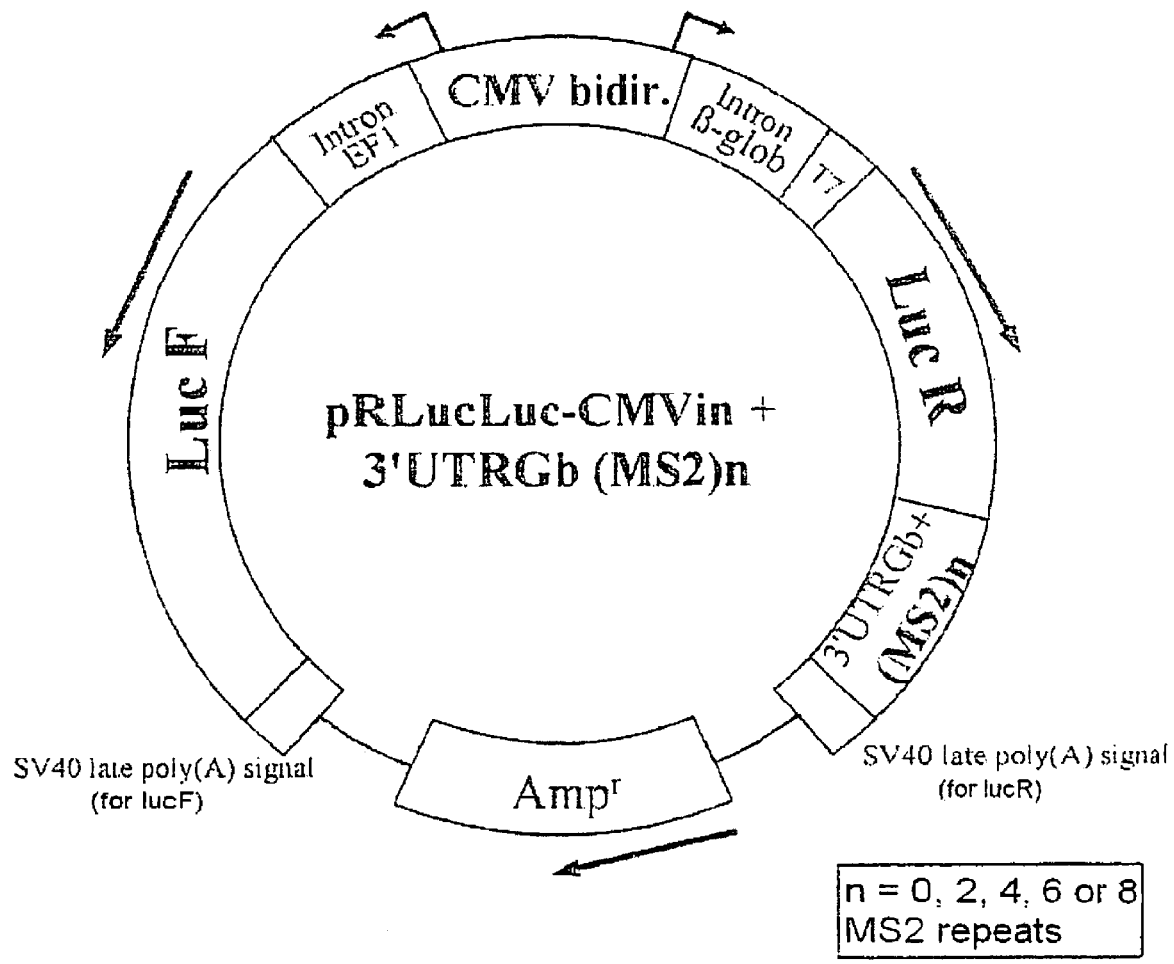

FIG. 3 is a diagram of the reporter vector pRLucLuc-CMVin+3'UTRGb (MS2)$_n$.

In the Figure, the bidirectional promoter CMV controls the expression of two open reading frames, (i) an open reading frame coding for luciferase R ("Luc R") and including a region 3'UTR containing eight copies of the nucleotide site MS2, a recognition site of the protein MS2CP and (ii) an open reading frame coding for the protein luciferase F ("LucF"), respectively.

The vector also includes a gene for ampicillin resistance ("Amp'"), placed under the control of the CMV promoter.

FIG. 4 illustrates the mode of operation of an expression system I.

Figure 4A:
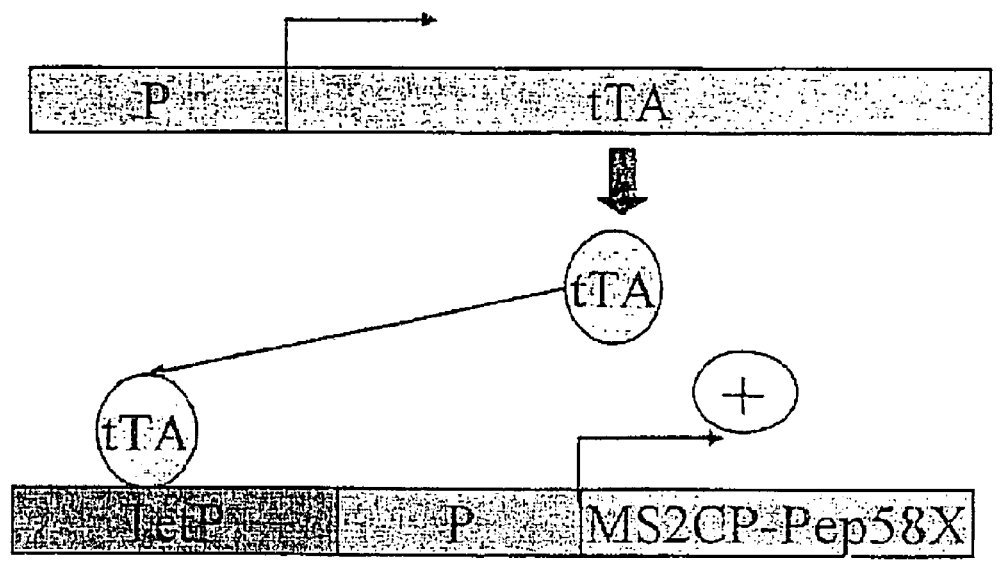

FIG. 4A illustrates the synthesis of the fusion polypeptide Pep58X-RNA binding protein when the promoter containing the TetP sequence is activated by the activating protein tTA, which is itself expressed constitutively.

Figure 4B:
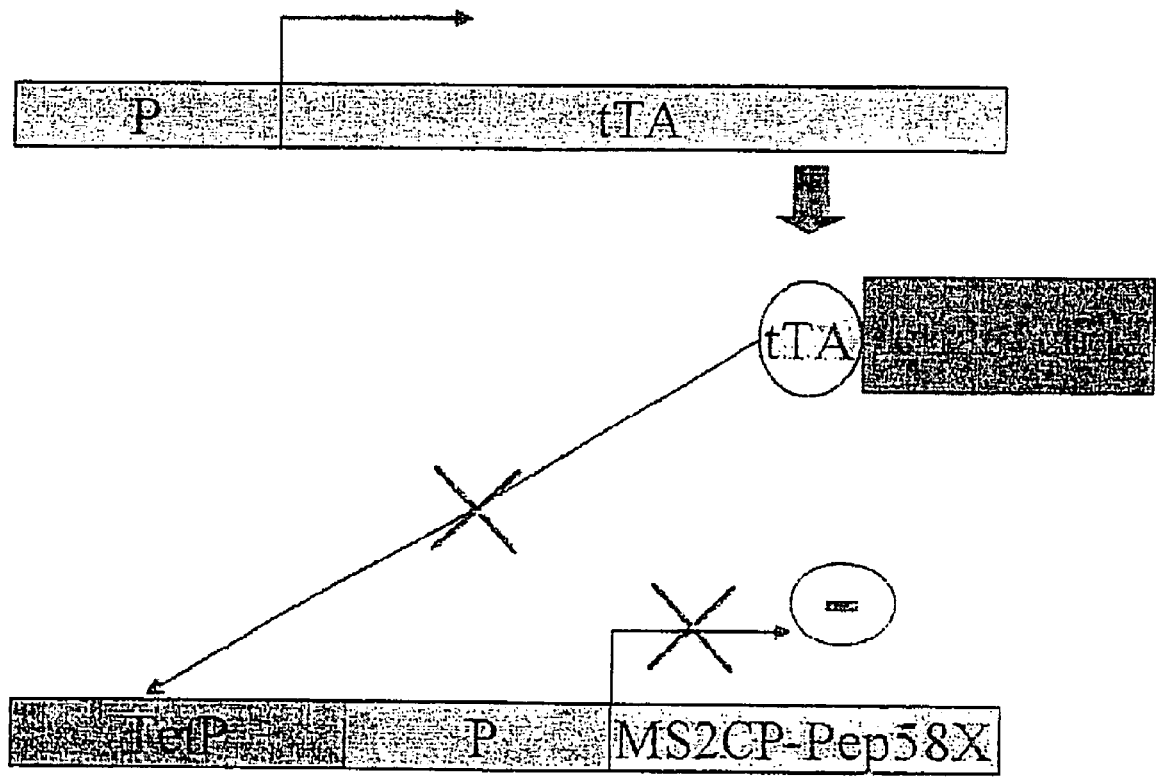

FIG. 4B illustrates the absence of production of the fusion polypeptide Pep58X-RNA binding protein in a situation in which the activating protein tTA is produced in the presence of tetracycline and does not activate the TetP sequence of the promoter controlling the expression of the gene Pep58X-RNA binding protein.

FIG. 5 illustrates the principle of operation of the expression system II.

Figure 5A:
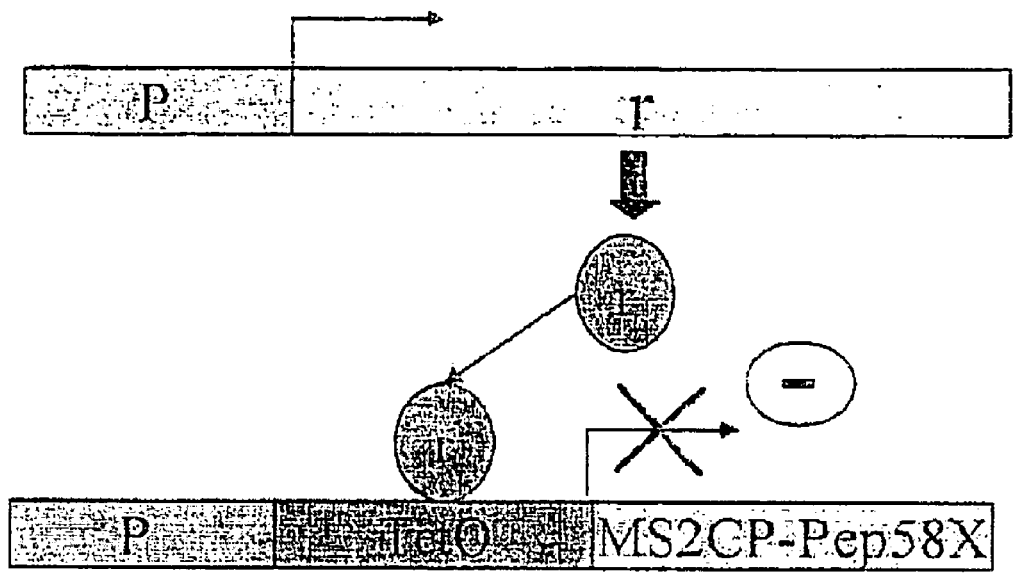

FIG. 5A illustrates the repression of the expression of the fusion polypeptide Pep58X-RNA binding protein under the inhibitory effect of the promoter containing the TetO sequence by the repressor protein Tet(r), which is itself expressed constitutively.

Figure 5B:
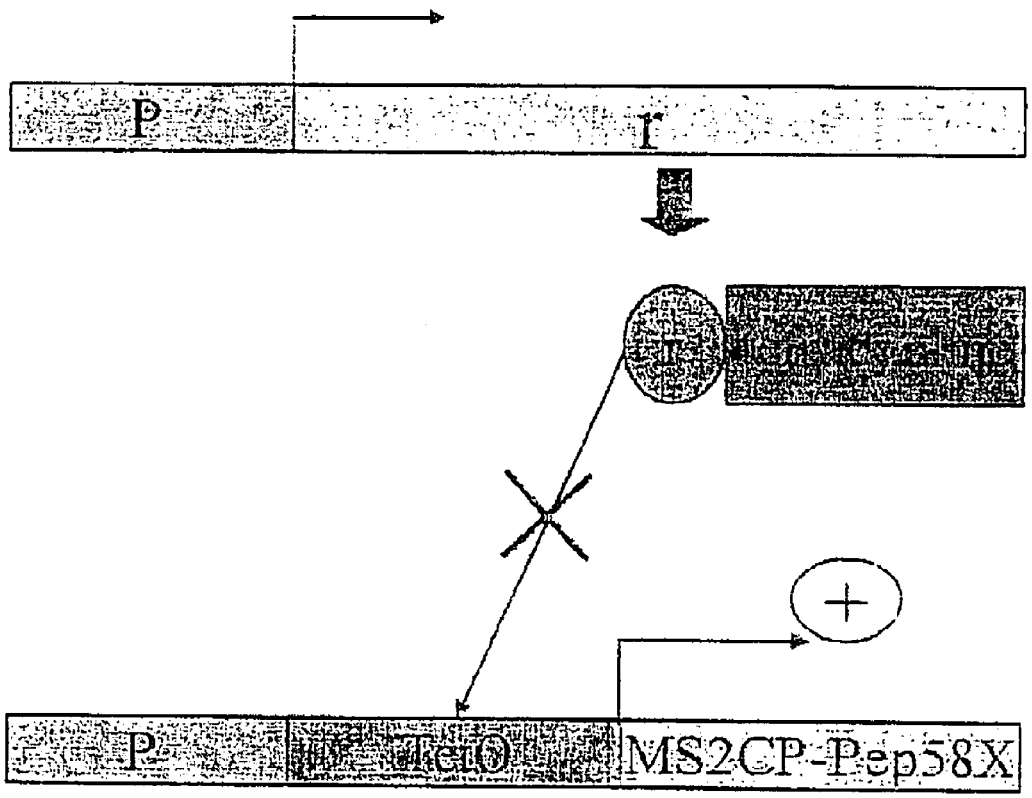

FIG. 5B illustrates the activation of the synthesis of the fusion polypeptide Pep58X-RNA binding protein when the repressor protein Tet(r) is placed in contact with tetracycine, which deactivates it and prevents it from inhibiting the promoter containing the TetO sequence.

FIG. 6 illustrates the results of inhibitory activity of a peptide inhibitor of the invention on the translation of the reporter protein CAT in *Xenopus*.

Figure 6A:
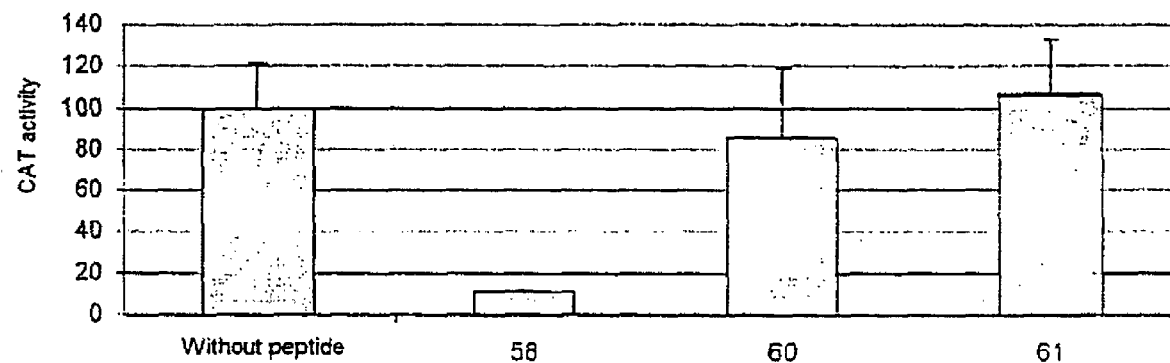

FIG. 6A: expression of CAT-B2 mRNA in the absence of peptide or in the presence of the peptides Pep58X ("58"), Pep60X ("60") and Pep61X ("61").

Figure 6B:
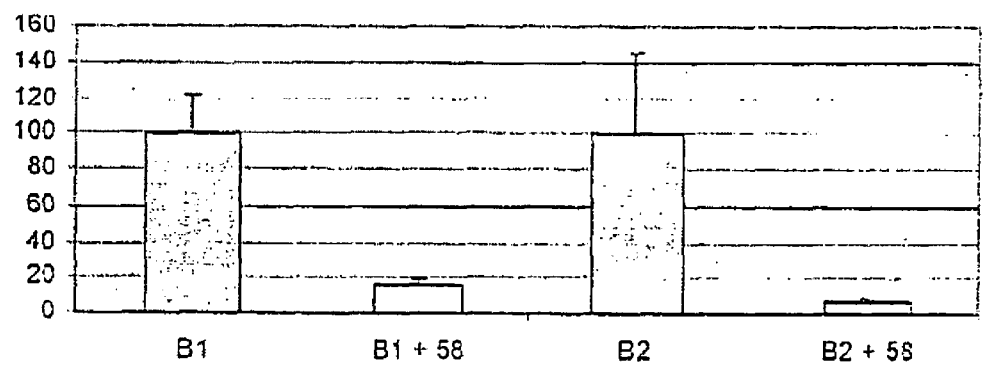

FIG. 6B: expression of the mRNAs CAT-B1 ("B1") and CAT-B2 ("B2") in the absence of peptide or in the presence of the peptide Pep58X ("B1+58" and "B2+58", respectively).

Along the abscissa: the identity of the peptide used (FIGS. 6A and 6B) and the identity of the CAT mRNA used (FIG. 6B)

Along the ordinate: CAT activity, expressed as percentage of the activity without peptide, the activity without peptide being fixed arbitrarily at 100%.

FIG. 7 illustrates the results of the translation of the marker protein luciferase by making use of a control system of translation including the vectors pMS2CP-Pep58X, pMS2CP (used as control) and the reporter vector pRLuc Luc CMVin+ 3'UTRgb (MS2)$_8$.

Along the abscissa: concentration of proteins expressed.

Figure 7A:
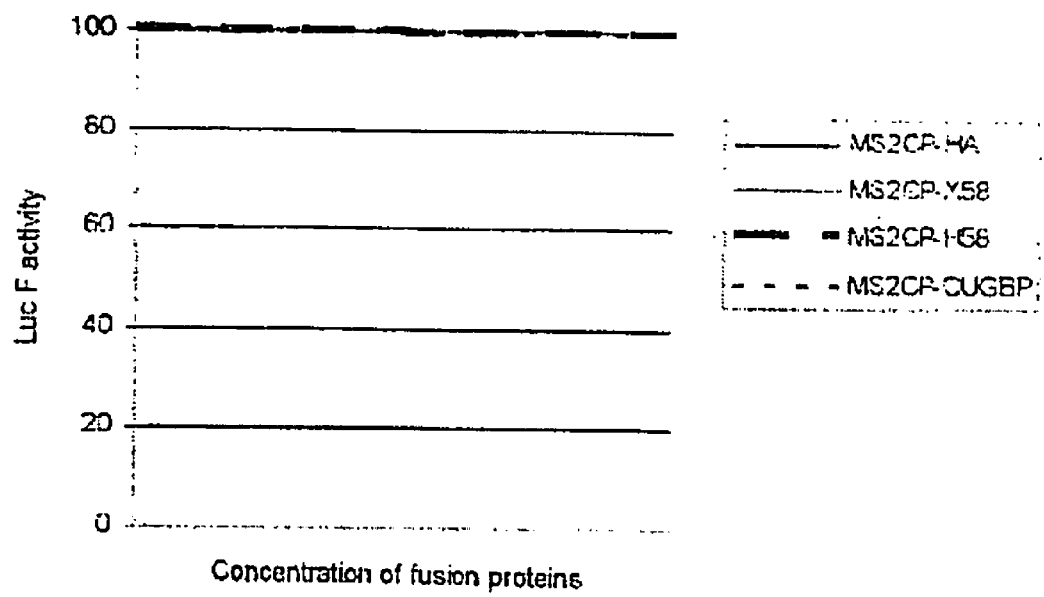
Figure 7B:
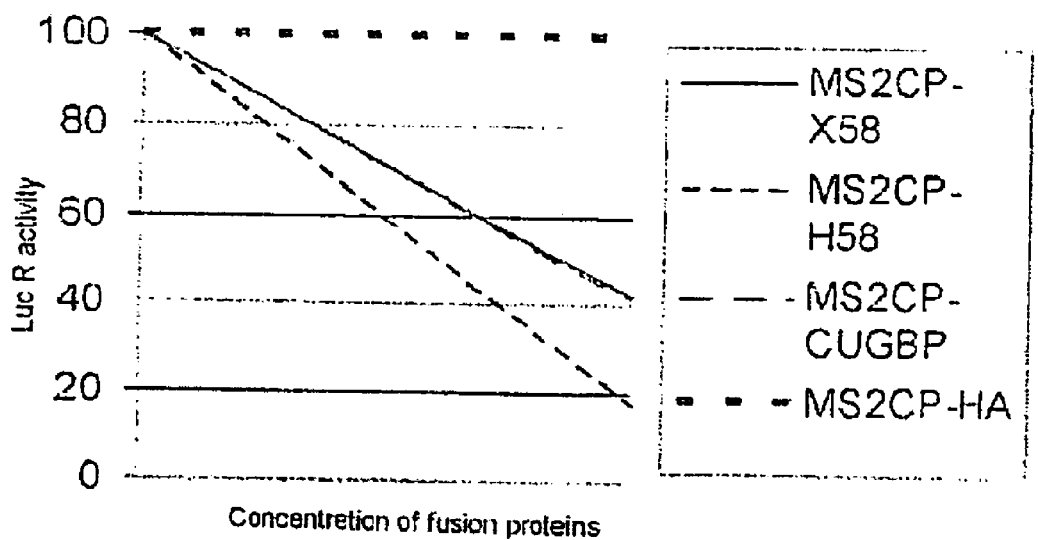

Along the ordinate: expression of Luc F (FIG. 7A) and Luc R relative to the expression of Luc F (FIG. 7B).

DETAILED DESCRIPTION OF THE INVENTION

It is shown according to the invention that a small family of peptides, which possess among themselves a high structural homology, has the capacity to inhibit the translation of proteins in cell systems.

More specifically, the applicant has shown that particular peptides derived from a specific region of the proteins EDEN-BP and CUG-BP, possessed an inhibitory activity towards the translation of proteins when these peptides are co-injected with a reporter mRNA into cells in culture.

Thus, it was shown according to the invention that a peptide of 28 amino acids possessing the amino acid sequence extending from the amino acid in position 183 to the amino acid in position 210 of the 489 amino acids long sequence of the protein EDEN-BP (SEQ ID No 9), derived from *Xenopus laevis*, possessed on its own the desired activity to inhibit the translation of proteins.

This first peptide of 28 amino acids is designated "Pep58X" for the purposes of the present description.

It was also shown according to the invention that a peptide possessing a very high degree of identity in terms of amino acids with the peptide inhibitor Pep58X defined above, the said peptide being designated Pep58H, also possessed the desired activity to inhibit the translation of proteins.

The peptide Pep58H consists of a peptide of 28 amino acids long possessing the amino acid sequence extending from the amino acid in position 183 to the amino acid in position 210 of the human protein CUG-BP.

It is shown in the examples that the level of inhibitory activity of Pep58X and Pep58H is very similar. It has also been shown that the level of inhibitory activity of Pep58H is identical with that observed for the complete protein CUG-BP.

On the contrary, it has also been shown according to the invention that other peptides 28 amino acids long and derived from the region of 84 amino acids extending from the amino acid in position 155 to the amino acid in position 238 of the protein EDEN-BP of sequence SEQ ID No 9 did not possess inhibitory activity towards the translation of proteins. This concerns, in particular, peptides designated Pep60X and Pep61X, respectively, in the examples.

Family of Non-Specific Peptide Inhibitors According to the Invention.

It has been shown according to the invention that the peptide of 28 amino acids derived from the protein EDEN-BP of *Xenopus laevis*, designated Pep58X in the present description, and which possesses the amino acid sequence SEQ ID No 1 is capable of inhibiting non-specifically the translation of reporter messenger RNAs coding for the enzyme CAT (chloramphenicol acetyl transferase).

Thus, the peptide Pep58X was co-injected with different reporter messenger RNAs into embryos of the amphibian *Xenopus* (*Xenopus laevis*). After expression of the reporter genes, protein extracts were prepared and the activity of the reporter gene was determined. The peptide Pep58X inhibits the translation of the reporter messenger RNAs coding for the enzyme CAT, whether the reporter messenger RNA construction also includes the nucleotide site EDEN for binding to the protein EDEN-BP or whether the reporter messenger RNA does not include a nucleotide site EDEN specific for the binding of the RNA to the protein EDEN-BP. Consequently, it is shown according to the invention that a peptide comprising the amino acid sequence SEQ ID No 1, as is the case for the peptide Pep58X, inhibits the translation of the cellular messenger RNAs generally and not specifically.

The non-specific general inhibitory activity of the translation of proteins demonstrated with the peptides Pep58X of sequence SEQ ID No 1 and Pep58H of sequence SEQ ID No 2, which between them possess a high identity of about 89.3% of the amino acid sequence, has enabled the applicant to define a restricted family of peptide inhibitors of the translation of proteins, which is described hereafter.

The size of the non-specific peptide inhibitors of the translation of the messenger RNAs into proteins according to the invention, which all possess a high identity in terms of the amino acid sequence with the peptide Pep58X, is up to 250 amino acids.

Although peptides longer than 250 amino acids might also possess inhibitory properties towards the translation of proteins, the applicant thinks, without wanting to be bound by any theory, that such large peptides are likely to possess a reduced inhibitory activity, in particular as a result of the creation of conformational constraints in the peptide.

Hence the subject of the invention is a peptide inhibitor of the translation of proteins, characterised in that its length is up to 250 amino acids and in that it comprises an amino acid sequence possessing at least 85% identity with the amino acid sequence SEQ ID No 1 of Pep58X.

The terms protein, polypeptide and peptide used in the present description are interchangeable and designate a linear chain of amino acid residues linked to each other by a peptide bond between the alpha amino group and the carboxyl group of two adjacent amino acid residues. Polypeptides containing at least one non-peptide linkage such as a retro-verso linkage (NH—CO), a carba linkage ($CH_2$—$CH_2$) or even a ketomethylene linkage (CO—$CH_2$) also form part of the invention.

A peptide inhibitor of the translation of proteins according to the invention comprises an amino acid sequence possessing preferably at least 86%, 87%, 88%, 89.3%, 90%, 91%, 92%, 93%, 94%, 95%, 96%, 97%, 98% or 99% identity in terms of amino acids with the peptide inhibitor of sequence SEQ ID No 1.

The "percentage identity" between two amino acid sequences in the sense of the present invention is defined by comparing the two sequences optimally aligned, through a window of comparison.

The part of the amino acid sequence in the window of comparison may thus comprise additions or deletions (for example "gaps") with respect to the reference sequence (which does not comprise these additions or deletions) so as to obtain an optimal alignment between the two sequences.

The percentage identity between the two amino acid sequences is calculated by determining the number of positions at which an identical amino acid residue is observed for the two sequences compared after alignment, then by dividing the number of positions at which there is identity between the two amino acid residues compared by the total number of positions in the window of comparison, then by multiplying the result by one hundred in order to obtain the percentage identity between the two amino acid sequences.

The optimal alignment of the sequences for the comparison can be achieved by means of a computer with the aid of known algorithms.

Preferably, the percentage of sequence identity is determined with the aid of the software CLUSTAL W (version 1.82) the parameters being fixed as follows: (1) CPU MODE="ClustalW mp; (2) ALIGNMENT="full"; (3) OUTPUT FORMAT="aln w/numbers"; (4) OUTPUT ORDER="aligned"; (5) COLOR ALIGNMENT="no" (6) KTUP (WORD SIZE)="default";(7) WINDOW LENGTH="default"; (8) SCORE TYPE="percent"; (9) TOPDIAG="default"; (10) PAIRGAP="default"; (11) PHYLOGENETIC TREE/TREE TYPE="one"; (12) MATRIX="default"; (13) GAP OPEN="default"; (14) END GAPS="default"; (15) GAP EXTENSION="default"; (16) GAP DISTANCES="default" (17) TREE TYPE="cladogram" and (18) TREE GRAP DISTANCES="hide".

The peptides belonging to the family of the peptide inhibitors of the translation of proteins according to the invention thus possess, in the case of some of them, an amino acid sequence containing one or more substitutions, additions or deletions of an amino acid with respect to the peptide inhibitors comprising the sequence SEQ ID No 1. An illustration of such peptides is the peptide inhibitor of sequence SEQ ID No 2.

The peptides whose amino acid sequence possesses one or more substitutions of an amino acid by an equivalent amino acid with respect to the peptide inhibitors of the translation of proteins such as defined in a general manner above form part of the invention.

By equivalent amino acids according to the present invention are meant amino acids which have an inhibitory activity of the same order of magnitude as the inhibitory activity of the reference peptide inhibitor, i.e. amino acids which, when they replace an amino acid present in the amino acid sequence of the reference peptide inhibitor have an inhibitory activity having the same order of magnitude as that of the reference peptide inhibitor.

As an illustration, conservative substitutions of amino acids are the replacements of an amino acid by another amino acid belonging to the same class. Thus, the aliphatic amino acids Ala, Val, Leu and Ile are interchangeable; so also are the amino acids possessing a hydroxyl residue such as Ser and Thr; so also are the amino acids Asp and Glu; so also are the amino acids possessing an amide function such as Asn and Gln; so also are the basic amino acids such as Lys and Arg; and so also are the aromatic amino acids such as Phe and Tyr.

The level of inhibitory activity of a peptide inhibitor according to the invention can easily be determined by the man skilled in the art, for example by calculating, for each concentration of a series of increasing intracellular concentrations of peptide inhibitor, the percentage expression of a marker protein encoded in a reporter mRNA, with respect to the level of expression of the said marker protein in the absence of the peptide inhibitor, then by calculating the slope of the straight line joining the different values of percentage expression of the marker protein for the different increasing values of concentration of the peptide inhibitor, as shown in detail in the examples.

The calculation of the slope of the straight line of inhibition can be made with the aid of the following formula:

$$P = \frac{d[\text{marker protein}]}{d[\text{peptide inhibitor}]},$$

in which

P is the value of the slope of the inhibition straight line;

d [marker protein] is the difference in the quantity of marker protein between the two concentrations of peptide a and b;

d [peptide inhibitor] is the difference between the two concentrations of peptide a and b.

According to the invention, a defined peptide inhibitor possesses a level of inhibitory activity of the translation of proteins of the "same order of magnitude" as the level of inhibitory activity of a reference peptide when the P value of the said defined peptide is included between −0.3 and −0.8, and preferably between −0.4 and −0.7, the P value being preferably about −0.6.

Peptides up to 250 amino acids length and which possess at least 85% identity in terms of amino acids with the amino acid sequence extending from the amino acid in position 156 to the amino acid in position 405 of the sequence of the protein EDEN-BP also form part of the invention, the protein EDEN-BP possesses the amino acid sequence referenced in the present description as the sequence SEQ ID No 9. The amino acid sequence 156405 comprised in the sequence SEQ ID No 9 of EDEN-BP consists of the amino acid sequence which is comprised between the second and the third RNA binding domains of the protein EDEN-BP.

Peptides maximally 100 amino acids long and which comprise at least 30 consecutive amino acids of the sequence of 84 amino acids extending from the amino acid in position 155 to the amino acid in position 238 of the sequence of the protein EDEN-BP, referenced as the sequence SEQ ID No 3, also form part of the invention, said peptides comprising an amino acid sequence possessing at least 85% identity in terms of amino acids with the sequence SEQ ID No 1.

Peptides maximally 100 amino acids long and which comprise at least 30 consecutive amino acids of the sequence of 88 amino acids extending from the amino acid in position 155 to the amino acid in position 242 of the sequence of the protein CUG-BP, referenced as the sequence SEQ ID No 4, also form part of the invention, said peptides comprising an amino acid sequence possessing at least 85% identity in terms of amino acids with the sequence SEQ ID No 2.

The applicant has in fact shown that the sequence SEQ ID No3 of 84 amino acids, derived from the protein EDEN-BP, interacts in the cell with the protein ePABP, known to be implicated in the mechanisms of regulation at the level of the translation of the messenger RNAs.

A peptide inhibitor of the translation of proteins such as defined above advantageously has a length up to 50 amino acids.

Preferentially, a peptide inhibitor of the translation of proteins according to the invention is characterised in that it has a length up to 30 amino acids and most preferably has a length up to 28 amino acids.

The short peptide inhibitors having a length up to 50 amino acids and, better still a length up to 30 amino acids are preferred owing to the fact that they are better able to penetrate cell membranes and thus act efficaciously and rapidly in the cytoplasm to inhibit the translation of the messenger RNAs.

A peptide inhibitor of the translation of proteins which is characterised in that it comprises an amino acid sequence possessing at least 89%, and preferably 89.3%, identity with the amino acid sequence SEQ ID No 1 forms part of the invention.

A peptide characterised in that it comprises the sequence SEQ ID No 1, in particular the peptide of sequence SEQ ID No 1 complies with the above definition of a peptide inhibitor.

A peptide characterised in that it comprises the sequence SEQ ID No 2, in particular the peptide of sequence SEQ ID No 2 also forms part of the above definition of a peptide inhibitor.

The invention also relates to a process for the production of a peptide inhibitor of the translation of proteins such as defined above, the said process comprising the steps of:

(a) insertion of a nucleic acid coding for the said peptide inhibitor into a suitable expression vector;

(b) cultivation in a suitable culture medium of a cell host transformed or transfected beforehand with the recombinant vector obtained in step (a);

(c) recovery of the conditioned culture medium or lysis of the cell host, for example by sonication or by osmotic shock;

(d) separation and purification of said peptide inhibitor from said culture medium or also from the cell lysates obtained in step (c);

(e) if necessary, characterisation of the recombinant peptide inhibitor produced.

The peptide inhibitors according to the invention may be characterised by fixation to an immunoaffinity chromatography column on which antibodies directed against the said peptide have been immobilised beforehand.

According to another feature, a peptide inhibitor according to the invention can be purified by passage through a suitable series of chromatography columns, according to methods known to the specialist skilled in the art and described for example in AUSUBEL et al. (1989). A peptide inhibitor according to the invention can also be prepared by the conventional procedures of chemical synthesis, equally well in solution or on a solid phase.

As an illustration, a peptide inhibitor according to the invention can be prepared by the procedure in homogeneous solution described by HOUBEN WEIL (1974) or also by the procedure of synthesis on a solid phase described by MERRIFIELD (1965a, 1965b).

The invention also relates to a nucleic acid comprising a polynucleotide coding for a peptide inhibitor of the translation of proteins such as defined above.

Preferably, the said nucleic acid is characterised in that it includes a regulatory polynucleotide under the control of which is placed the polynucleotide coding for said peptide inhibitor of the translation of proteins.

The invention also relates to a nucleic acid such as defined above, characterised in that it is inserted into a recombinant cloning or expression vector.

The invention also relates to a recombinant cloning or expression vector comprising a nucleic acid such as defined above.

Any suitable vector known or defined in the present description can be used.

The peptide inhibitors such as defined above are used to inhibit the translation of proteins non-specifically, preferably in cell systems, although the peptide inhibitors may also be used to inhibit the translation of proteins in cell-free systems, for example starting from a cell lysate, for example by incubating an extract of cell messenger RNA in a cell-free system constituted by a lysate of rabbit reticulocytes according to the conventional procedure which is described by UCHIDA et al. (2002). According to a preferred feature of the invention, the peptide inhibitors such as defined above are used in order to perturb cell metabolism to the extent of causing the death of the cells into which these peptide inhibitors have penetrated.

Thus, the peptide inhibitors of the translation of proteins such as defined above can be used to eliminate certain classes of cells against which they may be targeted, such as tumour cells.

For example, the peptide inhibitors according to the invention can be fused with a peptide or a protein or also coupled to a polysaccharide, the said peptide, the said protein or the said polysaccharide consisting of ligands specifically recognised by receptors expressed on the target cells, for example of the membrane surface of the target cells, the said target cells then internalising the peptide inhibitors which subsequently cause their death by blocking the translation of the cell proteins. Examples of peptides or proteins which can be fused with a peptide inhibitor according to the invention are, in particular, the antibodies or antibody fragments which specifically recognise antigens expressed specifically by certain classes of cells, such as tumour cells.

For example, it is possible to prepare a fusion protein between a peptide inhibitor according to the invention and an antibody or antibody fragment, for example an Fab fragment or also an F(ab')$_2$ fragment specifically recognising an antigen expressed selectively by the target tumour cells, such as for example the tumour antigen Tn well known in the state of the art. In vitro, the tumour cells present in a population of cells taken from a patient can thus be eliminated by incubation of the cells derived from the patient with suitable concentrations of the fusion protein peptide inhibitor-antibody (or antibody fragments), followed by recovery of the normal non-tumour cells.

It goes without saying that the fusion proteins peptide inhibitor-cell receptor ligand can also be used in vivo, for example in the context of anti-cancer therapies.

Specific Inhibitory Fusion Polypeptides of the Translation of Proteins.

According to another feature, the invention relates to fusion polypeptides capable of inhibiting specifically the translation of a target polynucleotide of interest to the corresponding protein, such a fusion polypeptide comprising a peptide inhibitor of the translation of proteins such as previously defined in the description, said peptide inhibitor being fused with an RNA binding protein specifically recognising a target nucleotide site of the messenger RNA which is targeted.

In fact, it has been shown according to the invention that a fusion polypeptide between the peptide Pep58X of sequence SEQ ID No 1 and the RNA binding protein MS2CP was capable of inhibiting specifically the translation of a messenger RNA comprising the target nucleotide site MS2 and an open reading frame coding for the marker protein luciferase, placed under the control of a suitable promoter.

Figure 1:
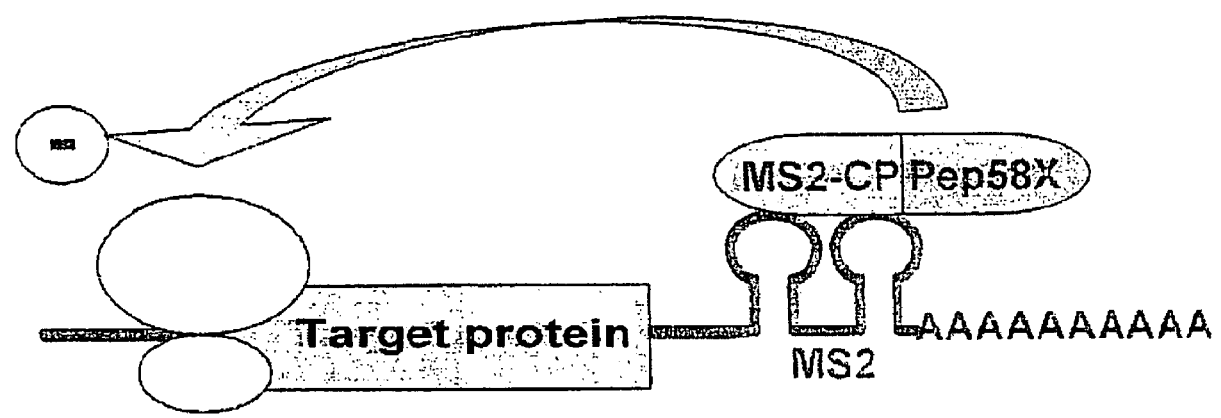
FIG. 1 illustrates the mode of action of a fusion polypeptide according to the invention comprising the peptide inhibitor Pep58X fused with the RNA binding protein MS2CP. The fusion polypeptide is designated "MS2CP-Pep58X". In the lower part of the Figure, a target messenger RNA is shown comprising a target nucleotide motif of the RNA binding protein MS2CP, which has been designated "MS2" and which is shown in the Figure by a stem-loop structure and an expression cassette of the target protein of interest. As shown in the Figure, the fused protein MS2CP makes possible the binding of the fusion polypeptide to the target messenger RNA at the level of the MS2 site, and this enables the peptide inhibitor Pep58X to exert its inhibitory biological activity specifically on the target messenger RNA (poly-A tail disclosed as SEQ ID NO: 17).
Figure 2:
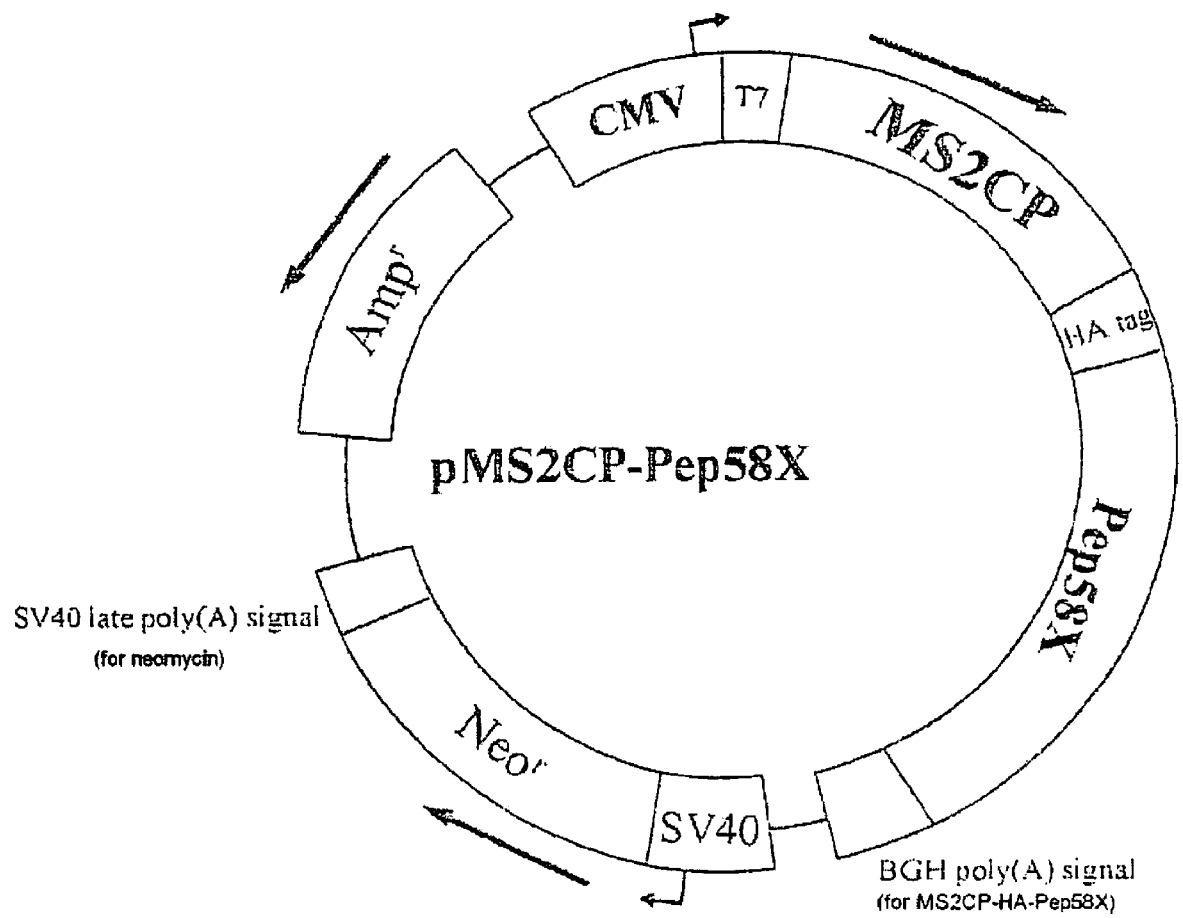
FIG. 2 is a diagram showing the map of the plasmid pMS2CP-Pep58X. On the vector, "CMV" designates the promoter of the cauliflower mosaic virus which controls the expression of the open reading frame coding for the fusion polypeptide between the RNA binding protein MS2CP and the peptide inhibitor Pep58X. In the Figure, the open reading frame codes for a fusion polypeptide in which the protein MS2CP and the peptide inhibitor Pep58X are separated by the peptide HA (sequence "YPYDVPDYA" [SEQ ID No 11] extending from amino acid 98 to amino acid 106 of the protein hemaglutinin HA1), which constitutes a label for the detection and purification of the fusion polypeptide. "T7" designates the promoter of the phage T7, which makes possible RNA synthesis in vitro.

As illustrated in FIG. 1, the protein MS2CP contained in the fusion polypeptide binds selectively to its target nucleotide site MS2, and this enables the peptide inhibitor Pep58X to specifically inhibit the expression of the messenger RNA or messenger RNAs containing the target nucleotide site MS2.

The same results have been reported by the applicant with a fusion polypeptide containing the peptide inhibitor Pep58H and the RNA binding protein MS2CP.

In a fusion polypeptide according to the invention, the RNA binding protein, which is fused with the peptide inhibitor of the translation of proteins defined above is selected preferably from MS2CP, N, IRP and U1A, listed in Table 1 below.

TABLE 1

Preferred binding proteins

| Binding protein | Reference |
|---|---|
| MS2 | J. Coller, N. Gray, M. Wickens, Genes Dev. 12 (1998) 3226-3235. Witherell, G., J. Gott, and O. Uhlenbeck. 1991. Specific interaction between RNA phage coat proteins and RNA. Prog. Nucleic Acids Res. Mol. Biol. 40: 185-220 |
| N | E. De Gregorio, T. Preiss, M. W. Hentze, EMBO J. 18 (1999) 4865-4874. Tan, R. & Frankel, A. D. (1994) Biochemistry 33, 14579-14585 |
| IRP | E. De Gregorio, J. Baron, T. Preiss, M. Hentze, RNA 7 (2001)106-113. Hentze M W; Kuhne L C. Proc Natl Acad Sci USA. 1996 Aug. 6; 93(16): 8175-82. Review. PMID: 8710843 |
| U1A | A. S. Brodsky, P. A. Silver, RNA 6 (2000) 1737-1749. |

Advantageously, the RNA binding protein selected is localised at the NH$_2$-terminus of the fusion polypeptide, although it may also be localised at the COOH-terminus of the said fusion polypeptide.

In the fusion polypeptide, the RNA binding protein may be fused directly to the peptide inhibitor, i.e. depending on the case:

(i) when the RNA binding protein is localised at the NH$_2$ terminus of the fusion polypeptide, the last amino acid in the COOH-terminal position of the RNA binding protein is chemically linked, preferably by a normal peptide linkage, to the amino acid localised at the NH$_2$-terminal position of the peptide inhibitor; or (ii) when the RNA binding protein is localised at the COOH-terminal position of the fusion polypeptide, the amino acid localised at the COOH-terminal position of the peptide inhibitor is linked directly, preferably by a normal peptide linkage, to the amino acid localised at the NH$_2$-terminal position of the RNA binding protein.

According to another embodiment of a fusion polypeptide according to the invention, the RNA binding protein and the peptide inhibitor of the translation of proteins are not linked to each other directly but, on the contrary, are separated from each other in the fusion polypeptide by a spacer, preferably a hydrophobic sequence of amino acids. The spacer sequence of amino acids possesses sufficient size to constitute a region of flexibility in the protein molecule making possible a relative mobility of the RNA binding protein with respect to the peptide inhibitor.

The spacer peptide is at least 3 amino acids long and at the most 50 amino aids long. Preferably the length of the spacer peptide is included between 5 and 30 amino acids, and most preferably between 5 and 20 amino acids.

Preferably, when the spacer sequence or the spacer peptide is hydrophobic, the said spacer sequence facilitates the penetration of the fusion polypeptide through the cell membranes. In this case, the said spacer peptide contains mainly hydrophobic amino acids such as the amino acids valine, leucine or also isoleucine.

In this embodiment, the sequence of the spacer peptide consists preferentially of at least 50% of hydrophobic amino acids, preferably of at least 60% and most preferably of at least 80% of hydrophobic amino acids.

According to a particular embodiment, the spacer peptide consists of a poly(alanine) chain of amino acids, comprising from 3 to 50, better still from 5 to 30, advantageously from 5 to 20 and most preferably from 5 to 10 alanine residues.

According to another feature, the spacer sequence of amino acids or the spacer peptide constitutes a tag that makes possible the detection or even the purification of the fusion polypeptide present in a sample. For example, the spacer peptide may be constituted of the peptide "HA TAG", of sequence SEQ ID No 11, as described in the examples.

Specific and illustrative examples of specific inhibitory fusion polypeptides according to the invention are constituted by:

fusion polypeptide MS2CP-HA TAG-Pep58X of amino acid sequence SEQ ID No 5, which is encoded in the nucleic acid of sequence SEQ ID No 7.

fusion polypeptide MS2CP-HA TAG-Pep58H of amino acid sequence SEQ ID No 6, which is encoded in the nucleic acid of sequence SEQ ID No 8.

The invention also relates to a nucleic acid comprising a polynucleotide coding for a fusion polypeptide such as defined above.

The preferred nucleic acids according to the invention are the following:

the nucleic acid of sequence SEQ ID No 7 coding for the fusion polypeptide MS2-HA TAG-Pep58X;

the nucleic acid of sequence SEQ ID No 8 coding for the fusion polypeptide MS2CP-HA TAG-Pep58H.

According to a preferred feature, the nucleic acid coding for a fusion polypeptide according to the invention is characterised in that it comprises a regulatory polynucleotide under the control of which is placed the polynucleotide coding for the fusion polypeptide.

Most preferably, the said nucleic acid is characterised in that the regulatory polynucleotide is an inducible regulatory polynucleotide.

In fact, in practice, the control of the translation of certain pre-defined target proteins by a specific inhibitory fusion polypeptide according to the invention requires that at defined times of a cell culture, for example in a bioreactor, the target protein(s) is/are not produced, whereas at other times, on the contrary, the production of the target protein(s) is desired.

The invention also relates to a nucleic acid coding for a specific inhibitory fusion polypeptide such as defined above, characterised in that it is inserted into a cloning or expression vector.

The invention also relates to a recombinant cloning or expression vector, characterised in that it comprises a nucleic acid coding for a specific peptide inhibitor such as defined above.

Any cloning or expression vector known or described in the present invention can be used.

The specific inhibitory fusion polypeptides as well as the nucleic acids coding for these fusion polypeptides of the invention have enabled the applicants to devise control systems for the translation of one or more target polynucleotides of interest, the technical characteristics of these control systems being defined below.

Control Systems for the Translation of One or More Target Nucleotides of Interest.

According to another feature, the invention relates to fusions between peptide and oligonucleotide capable of inhibiting specifically the translation of a target polynucleotide of interest into the corresponding protein. Such a fusion molecule comprising a peptide inhibitor of the translation of proteins such as previously defined in the description, said peptide inhibitor being fused with an oligonucleotide specifically recognising a target nucleotide site of an mRNA which is the target. An example of this type of oligonucleotide is Aptastruc described in the PCT application N° PCT/FR 95/01036.

The specific inhibitory fusion polypeptides of the translation of proteins such as defined above may be integrated into various control systems for the translation of one or more target polynucleotides of interest.

A first control system for the translation of one or more target polynucleotides of interest comprises of a nucleic acid coding for a peptide inhibitor-RNA binding protein fusion polypeptide such as defined above.

A second control system of the invention consists of a control system which comprises a peptide inhibitor-RNA binding protein fusion polypeptide such as defined above.

When the nucleic acid coding for the fusion polypeptide, optionally in the form of a DNA insert in a recombinant vector, is used to transfect the cells in which the control of translation is desired, the fusion polypeptide is expressed, optionally in an inducible manner. When the fusion polypeptide is expressed in the cells thus transfected, the said fusion polypeptide binds specifically to the target messenger RNAs which comprise the target nucleotide site of the RNA binding protein contained in the said fusion polypeptide, owing to which the said fusion peptide inhibits the translation of the proteins encoded in the said target messenger RNAs.

Similarly, when the specific inhibitory fusion polypeptide is placed in contact with the target cells, the said fusion polypeptide is internalised in the cytoplasm of these cells and inhibits the translation of the proteins encoded in the target messenger RNAs containing in their sequence, the target nucleotide site of the RNA binding protein contained in the said fusion polypeptide.

According to a third control system of the translation of one or more target polynucleotides of interest according to the invention, the said control system comprises, on the one hand, a nucleic acid coding for the specific inhibitory fusion polypeptide and, on the other, a second nucleic acid which constitutes the target nucleic acid of the fusion polypeptide and which codes for the protein of interest, the control of the translation of which is desired.

Thus, the subject of the invention is also a control system of the translation of a target polynucleotide of interest comprising:

(a) a first nucleic acid consisting of a nucleic acid comprising a polynucleotide coding for a specific inhibitory fusion polypeptide such as defined in the present description;

(b) a second nucleic acid comprising:

(i) at least one copy of a target nucleotide sequence of the RNA binding protein contained in the fusion polypeptide encoded in the first nucleic acid such as defined in (a); and (ii) the polynucleotide of interest, the control of the translation of which is desired.

Most preferably, the third control system according to the invention above is characterised in that the second nucleic acid which codes for the protein of interest, the control of the translation of which is desired, comprises a regulatory polynucleotide under the control of which is placed the polynucleotide of interest coding for the said protein of interest.

A fourth control system of the translation according to the invention consists of a control system of the translation of a target polynucleotide of interest which comprises:
- (a) a peptide inhibitor-RNA binding protein fusion polypeptide such as previously defined in the description;
- (b) a nucleic acid comprising:
  - (i) at least one copy of a target nucleotide sequence of the RNA binding protein contained in the fusion polypeptide such as defined in (a); and
  - (ii) the polynucleotide of interest, the control of the translation of which is desired.

Preferably, the nucleic acid (b) of the control systems of the translation of proteins defined above comprises at least 2 copies, advantageously at least 3 or 4 copies of the target nucleotide sequence of the RNA binding protein contained in the fusion polypeptide of the invention. Advantageously, the nucleic acid (b) contains 5, 6, 7, 8, 9, 10, 11, 12, 13, 14, 15, 16, 17, 18, 19, 20, 21, 22, 23 or 24 copies of the said target nucleotide sequence. In certain cases, the nucleic acid (b) thus contains up to 24 copies of the said target nucleotide sequence.

The invention also relates to a control system such as defined above, characterised in that the nucleic acid(s) which is/are included in the latter is/are inserted in a recombinant expression vector.

The invention also relates to a control system such as defined above, characterised in that the nucleic acid (b) is inserted in the genome of a prokaryotic or eukaryotic host cell.

The third and fourth translation control systems according to the invention makes it possible to regulate in a controlled manner the expression of a gene artificially inserted beforehand in a cell, said gene being preferably a gene coding for a protein, the synthesis of which must be controlled.

For example, in the field of the production of proteins of interest in bioreactors, there exists a recurrent problem linked to the toxicity of the protein of interest that it is desired to express towards the cells in the growth phase. In this application, the control system of the translation of proteins such as defined above makes possible, as a result of the presence of the fusion polypeptide, the repression of the expression of a target polynucleotide of interest during the growth phase of the cells, then if desired the expression of the protein of interest, once the plateau of cell growth has been attained within the reactor.

Compared with other existing control systems which act at the level of transcription of RNA synthesis and of which great inertia of response is consequently observed, as for example the system TeT on/TeT off, the control system according to the invention allows a rapid response of repression or, on the contrary, activation of the synthesis of the target proteins.

As can be understood, the entire potentiality of the control system of the translation of proteins according to the invention is attained when the expression of the peptide inhibitor-RNA binding protein fusion polypeptide is inducible: thus, repression of the synthesis of the said fusion polypeptide will allow the translation of the target polynucleotide of interest into the corresponding protein, whereas activation of the expression of the fusion polypeptide will inhibit the translation of the target polynucleotide of interest into the corresponding protein.

Thus, in order to pursue the objective of the invention, it is hence particularly advantageous to use nucleic acid constructions in which the polynucleotide coding for the fusion polypeptide of the invention is placed under the control of an inducible regulatory polynucleotide, the time of the activity of which can be controlled.

According to another feature of the invention, the fusion polypeptides are used in the context of a targeted antiviral treatment by using, as RNA binding protein, a protein which binds specifically to nucleotide sequences of viral mRNAs.

Inducible Expression System of the Fusion Polypetide, Constitutive for the Control Systems of the Translation of Proteins According to the Invention.

The invention hence also relates to a nucleic acid comprising a polynucleotide coding for a peptide inhibitor-RNA binding protein fusion polypeptide such as defined above and which also includes a regulatory polynucleotide sensitive to the direct or indirect action of an inducing signal, consequently designated inducible regulatory polynucleotide.

Usable inducible systems of regulation according to the invention are shown in FIGS. 4 and 5, respectively.

Other inducible systems of regulation, based on principles of regulation identical with those shown in FIGS. 4 and 5 may also be used.

The inducible systems of regulation listed in Table 2 are preferred.

Most preferably, a nucleic acid coding for a fusion polypeptide according to the invention as well as a nucleic acid comprising (i) at least one copy of a target nucleotide sequence of the RNA binding protein contained in the said fusion polypeptide and (ii) the polynucleotide of interest, the control of the translation of which is desired, are inserted in a recombinant cloning or expression vector.

Vectors According to the Invention

By "vector" in the sense of the present invention, is meant a circular or linear DNA or RNA molecule, which is either single-strand or double-strand.

A recombinant vector according to the invention is preferably an expression vector.

In particular, it may be a vector of bacterial or viral origin.

In all cases, the nucleic acid coding for the peptide inhibitor-RNA binding protein fusion polypeptide according to the invention is placed under the control of one or more sequences containing regulatory signals for its expression in the cells under consideration, whether the regulatory signals are all contained in the nucleic acid coding for the said fusion polypeptide, or whether one or more or even all of the regulatory signals are contained in the recipient vector in which the nucleic acid coding for the fusion polypeptide has been inserted.

A recombinant vector according to the invention advantageously comprises suitable sequences for the initiation and termination of transcription.

In addition, the recombinant vectors according to the invention may include one or more functional origins of replication in the host cells in which their expression is desired as well as, if necessary, marker nucleotide selection sequences.

The recombinant vectors according to the invention may also include one or more regulatory expression signals such as defined above in the description, including inducible regulatory polynucleotides.

The preferred bacterial vectors according to the invention are for example the pBR322 (ATCC N° 37017) vectors or also the vectors such as pAA223-3 (Pharmacia, Uppsala, Sweden) and pGEM1 (Promega Biotech, Madison, Wis., USA). Mention may also be made of other commercially available vectors such as the vectors pQE70, qQE60, Pqe9 (QUIAGEN), psiX174, pBluescript SA, pNH8A, pMH 16A, pMH 18A, pMH46A, pWLNEO, pSV2CAT, pOG44, pXTI and pSG (Stratagene).

Preferably, an expression vector of a specific inhibitory fusion polypeptide such as previously defined is the vector pMS2CP-PEP58X deposited with the Collection Nationale de Cultures de Microorganismes on 8 Jul. 2003 under the access number I-3067.

A preferred vector comprising the nucleic acid containing (i) at least one copy of a target nucleotide sequence of the RNA binding protein contained in the specific inhibitory fusion polypeptide and (ii) the polynucleotide of interest, the control of the translation of which is desired is the vector pRLucLuc-CMVin+3'UTRGb (MS2)n, which is described in the examples.

The preferred eukaryotic expression vectors are those described in Makrides et al. (1999).

Transformed Host Cells According to the Invention

In general, a specific inhibitory fusion polypeptide of the translation of proteins according to the invention is used to inhibit specifically the translation of one or more proteins of interest in cells. For the implementation of the translation control systems such as defined above, it is thus necessary to transfect the target cells beforehand with a nucleic acid or a recombinant vector permitting the expression, if possible inducible, of the said fusion polypeptide in these target cells.

Thus, the subject of the present invention is also a host cell transformed by a nucleic acid coding for a specific inhibitory fusion polypeptide according to the invention, or by a recombinant vector in which such a nucleic acid is inserted.

The transformed host cell may be of bacterial or fungal origin or also any other eukaryotic cells.

However, the host cell is most preferably a mammalian cell, including a human cell.

Similarly, included in the invention are prokaryotic and eukaryotic host cells which comprise a control system for the translation of proteins such as previously defined, namely:
  a nucleic acid coding for a specific inhibitory fusion polypeptide of the translation of proteins according to the invention;
  a nucleic acid comprising the polynucleotide of interest, the control of the translation of which is desired and that also comprises the target nucleotide site of the RNA binding protein contained in the fusion polypeptide.

In certain cases, an attempt should first be made to integrate the target polynucleotide of the specific inhibitory fusion polypeptide envisaged into the genome of the transformed prokaryotic or eukaryotic host cell so as to obtain a stable cellular control system for the translation of the target protein(s) of interest.

In this particular embodiment, the control system such as previously defined is characterised in that the nucleic acid (b) is inserted in the genome of the prokaryotic or eukaryotic host cell.

Procedures and Kits According to the Invention

The subject of the invention is also a process for the in vitro control of the translation of a target polynucleotide of interest, characterised in that it comprises the following steps:

a) into a prokaryotic or eukaryotic host cell are introduced a nucleic acid comprising:
  (i) at least one copy of a target nucleotide sequence of an RNA binding protein;
  (ii) the polynucleotide of interest; and
  (iii) a regulatory polynucleotide under the control of which is placed the said polynucleotide of interest.

b) the recombinant host cell obtained at the end of step a) is cultivated in a suitable culture medium, the recombinant host cell expressing the said polynucleotide of interest;

c) when desired, the expression of the said polynucleotide of interest is inhibited by adding to the culture medium a specific inhibitory fusion polypeptide such as defined in the present description.

The subject of the invention is also a procedure for controlling the translation of a target polynucleotide of interest in vitro, characterised in that it comprises the following steps:

a) into a prokaryotic or eukaryotic host cell are introduced:
  (1) a nucleic acid comprising:
    (i) at least one copy of a target nucleotide sequence of an RNA binding protein;
    (ii) the polynucleotide of interest; and
    (iii) a regulatory polynucleotide under the control of which is placed the said polynucleotide of interest and
  (2) a nucleic acid comprising a polynucleotide coding for a specific inhibitory fusion polypeptide according to the invention placed under the control of an inducible regulatory polynucleotide;

b) the prokaryotic or eukaryotic host cell is cultivated in a suitable culture medium;

c) when desired, an agent permitting the activation or repression of the expression of the polynucleotide coding for the fusion polypeptide is added to the culture medium to give a suitable final concentration.

In reference to Table 2 as well as to FIGS. 4 and 5, the activating agent may consist of:
  tetracycline, when the inducible regulatory polynucleotide comprises the sequence TetO,
  tetracycline, when the inducible regulatory polynucleotide comprises the sequence TetP.

The subject of the invention is also a kit for the control of the translation of a polynucleotide of interest, characterised in that it comprises a specific inhibitory fusion polypeptide such as defined previously.

The invention also relates to a kit for the control of the translation of a polynucleotide of interest, characterised in that it comprises:
  (a) a specific inhibitory fusion polypeptide such as previously defined; and
  (b) a recombinant vector in which is inserted a nucleic acid comprising:
    (i) at least one copy of a target nucleotide sequence of the RNA binding protein contained in the fusion polypeptide such as defined in (a);
    (ii) the polynucleotide of interest The invention also relates to a kit for the control of the translation of a polynucleotide of interest, characterised in that it comprises a recombinant vector in which is inserted a nucleic acid comprising a polynucleotide coding for a specific inhibitory fusion polypeptide, preferably placed under the control of a regulatory polynucleotide, most preferably under the control of an inducible regulatory polynucleotide.

The invention also relates to a kit for the control of the translation of a polynucleotide of interest, characterised in that it comprises:
(a) a recombinant vector in which is inserted a nucleic acid comprising a polynucleotide coding for a specific inhibitory fusion polypeptide according to the invention, optionally placed under the control of a regulatory polynucleotide, most preferably placed under the control of an inducible regulatory polynucleotide; and
(b) a recombinant vector in which is inserted a nucleic acid comprising:
  (i) at least one copy of a target nucleotide sequence of the RNA binding protein contained in the fusion polypeptide such as defined in (a);
  (ii) the polynucleotide of interest.

According to a first advantageous feature, the kit such as defined above is characterised in that the recombinant vector (a) is the vector pMS2CP-PEP58X deposited with the Collection Nationale de Cultures de Microorganismes on 8 Jul. 2003 under the access number I-3067.

The invention also relates to the use of a control system of the translation of proteins such as defined in the present description or of a kit such as defined above for the control of the translation of a polynucleotide of interest.

According to a first feature, the above use is characterised in that the polynucleotide of interest is expressed in a cell-free system.

According to a second advantageous feature, the above use is characterised in that the polynucleotide of interest is expressed in vitro by cells cultivated in a bioreactor.

Pharmaceutical Compositions According to the Invention

The subject of the invention is also a pharmaceutical composition comprising a specific inhibitory fusion polypeptide for the translation of proteins such as defined in the present description.

The invention also relates to a pharmaceutical composition comprising:
(a) a specific inhibitory fusion polypeptide for the translation of proteins such as defined in the present description; and
(b) a recombinant vector in which is inserted a nucleic acid comprising:
  (i) at least one copy of a target nucleotide sequence of the RNA binding protein contained in the fusion polypeptide such as defined in (a);
  (ii) the polynucleotide of interest.

The invention also relates to a pharmaceutical composition comprising a recombinant vector in which is inserted a nucleic acid comprising a polynucleotide coding for a specific inhibitory fusion polypeptide for the translation of proteins according to the invention, optionally placed under the control of a regulatory polynucleotide, preferably an inducible regulatory polynucleotide.

The invention also relates to a pharmaceutical composition comprising:
(a) a recombinant vector in which is inserted a nucleic acid coding for a specific inhibitory fusion polypeptide such as defined in the present description, optionally placed under the control of a regulatory polynucleotide, preferably an inducible regulatory polynucleotide; and
(b) a recombinant vector in which is inserted a nucleic acid comprising:
  (i) at least one copy of a target nucleotide sequence of the RNA binding protein contained in the fusion polypeptide such as defined in (a);
  (ii) the polynucleotide of interest.

In cell therapy, the control systems for the translation of proteins according to the invention advantageously replace the inducer-regulator couple presently used by a unique molecule, the specific inhibitory fusion polypeptide such as defined previously, which is capable of modulating directly and very specifically the expression of a gene coding for a protein of therapeutic interest. With the control systems of the invention, the regulation of the expression of the gene(s) of interest is achieved post-transcriptionally in the cytoplasm of the host cells, and this enables the inducer to act rapidly and reversibly.

For an application of the control systems according to the invention to the direct correction of certain defects of expression of cellular genes ("regulomic" therapy), the specific inhibitory fusion polypeptide should contain a protein binding specifically to the target cellular messenger RNA. A cellular specificity of this type can be obtained in addition if the target messenger RNA is only expressed in a given cell type and/or if the specific inhibitory fusion polypeptide used only interferes with specific regulators of this cell type.

In antiviral or antiparasitic therapy, the drugs used at present often have adverse collateral effects linked to a lack of specificity of action. The targets of these drugs are found to include cellular proteins like the polymerases. On the other hand, a specific inhibitory fusion polypeptide according to the invention is capable of acting directly and specifically on the messenger RNAs derived from the viral genome and not on the products encoded in the genome of the infected cell. In fact, the constitutive RNA binding protein of the specific inhibitory fusion polypeptide of the invention is selected on the basis of its specificity for the viral messenger RNA that it is desired to neutralise. This strategy makes it possible to obtain a very high targeting specificity of the specific inhibitory fusion polypeptide of the invention. In addition, since it is understood that the expression of the viral proteins is regulated to a very large extent post-transcriptionally, a specific inhibitory fusion polypeptide according to the invention is particularly well adapted to antiviral control.

Similarly, as already mentioned, in the field of the production of proteins of interest in a bioreactor, the recurrent problem of toxicity for the cells of the protein of interest, the expression of which is desired, may be overcome by repressing the expression of the gene of interest by means of the specific inhibitory fusion polypeptides of the invention during the growth phase of the cells, then the gene coding for the protein of interest is activated to produce during the subsequent phases, for example once the cells have reached a stationary phase of growth. In addition, by acting on the concentration of the specific inhibitory fusion polypeptide present in the reaction medium, it may be possible to fine tune the expression of the gene of interest during all the steps of the production process in the bioreactor.

Furthermore, the present invention is illustrated in a non-limiting fashion by the following examples.

EXAMPLES

Example 1

Construction Protocol for the Recombinant Vectors MS2CP-Pep58X and MS2CP-Pep58H

The amplimers corresponding to Pep58X and Pep58H obtained by using as matrix respectively the plasmid pT7TSEDENBP (oligonucleotides ATGCTAGCGTAAAGT-TCGCAGACACTCAGAAAG [SEQ ID N 12] and ATGCG-GCCGCTGCATTGAGCTGCTGCATTTGC) [SEQ ID No 13] and the plasmid pT7TSCUGBP (oligonucleotides ATGCTAGCGTAAAATTTGCTGATACACAGMG [SEQ ID No 14] and ATGCGGCCGCTGCGCTGATTTGCTG-CATCTGC [SEQ ID No 15])(Paillard, 2002) are digested with NheI and XhoI and inserted into the vector pMS2CP-HA digested beforehand with NheI and XhoI. The vector pMS2CP-HA was obtained by insertion of the tag HA (TAC-CCATACGATGTTCCAGATTACGCT [SEQ ID No 16]) into the vector pcNMS2 (Lykke Andersen, Cell (103) 1121-31).

Example 2

Construction Protocol for the Vector pRLucLuc-CMVin+3' UTRGb (MS2)n

The plasmid pRL-Null (Promega) digested with XbaI is linked to hybridised oligos in order to obtain the plasmid pRLuc-XbI. The plasmid pGL3-Basic (Promega) is digested with BamHI/HindIII to release the insert SV40-Luc+ which is subcloned into the vector pRL-XbI digested with BamHI/HindIII to obtain the plasmid pRLuc-Luc.

A fragment containing the bidirectional promoter CMV and the introns b-globin and EF-1 (Généthon, Evry) is inserted into the XbaI/MiuI sites of pRLucLuc to produce the plasmid pRLucLucCMVin. The fragment containing the 3' untranslated b globin and 8 MS2 repeats obtained by NotI/ApaI digestion of the plasmid pGB (8MS2) (Lykke Andersen, Cell (103) 1121-31) is inserted into pRLucLuc linearised by PvuII to produce the plasmid pRLucLuc-CMVin+3'UTRGb (MS2)8.

Example 3

Characterisation of the Activity of a Peptide Inhibitor According to the Invention A. Materials and Methods The inhibitory activity of the peptides Pep60X and Pep61X of 17 and 28 amino acids, which correspond to the amino acids 211-227 (Pep60X) and 222-238 (Pep61X) respectively of the sequence of the protein EDEN-BP was tested.

The mRNAs used were prepared from the constructions described in Ezzedine et al., 2001. One femtomole of CAT-Eg2Delta2 mRNA, which does not contain an EDEN sequence in its untranslated 3', was co-injected with 200 ng of peptide into *Xenopus* embryos at the 2 cell stage.

After incubation for 4.5 hours, five batches of three embryos were collected for each injection series and protein extracts were prepared in order to measure the CAT activity.

B. Results

The corresponding results are presented in FIG. 6.

The mean and the standard deviation of the measurements made are presented in FIG. 7A. Only the peptide Pep58X demonstrated a significant inhibitory activity to the expression of CAT-Eg2Delta mRNA. The experiment was repeated with mRNAs containing an EDEN sequence, produced from the plasmid pEg2-Delta. The co-injection of Pep58X induced a translational repression similar to the pEg2-Delta 1 and pEg2-Delta 2 mRNAs (FIG. 6B).

Example 4

Functional Characterisation of the Specific Inhibitory Fusion Polyeptide MS2CP-Pep58X in Mammalian Cells Ex Vivo A. Material and Methods The cells were co-transfected with one of the vectors of the pMS2CP and the reporter vector.

The levels of translation of Renillia (R) luciferase and Firefly (F) luciferase were determined by luminiscence measurement (Promega's Dual Luciferase® Assay System).

The quantity of fusion proteins produced was evaluated by Western blot (anti HA polyclonal antibody, Santa Cruz Biotechnology) and standardised with respect to the quantity of a ubiquitous cell protein, the protein PCNA (Anti-Proliferating Cell Nuclear Antigen (PCNA) monoclonal antibody, Sigma Aldrich Company). The Luc F mRNA does not contain an MS2 site in its untranslated 3' part and should not be affected by the expression of MS2CP-Pep58X. In order to verify this, the expression of Luc F in the presence of MS2PC-Pep58X is analysed by the calculation d(LucF)/d (concentration of MS2CP-Pep58X).

The results are presented FIG. 7A. The slope of the straight line obtained is close to one (0.998), confirming that the fusion protein produced does not affect the expression of luciferase F. The expression of Luc F was then used as internal standard to estimate the effect of the fusion protein on the translation of Luc R mRNA. This latter contains, in fact, in its untranslated 3' part the MS2 sites permitting the binding of the protein MS2CP-Pep58X.

The results were analysed by the calculation d(R/F)/d(concentration of MS2CP-Pep58X) (FIG. 7B). The experiment was performed in parallel with MS2CP, the values obtained with MS2CP correspond to one hundred percent expression of Luc R.

B. Results

The results are presented in FIG. 7, which illustrates the results of the translation of the luciferase marker protein by making use of a control system for protein translation including the vectors pMS2CP-Pep58X, pMS2CP (used as reference) and the reporter vector pRLucLucCMVin+3'UTRGb (MS2)8

The expression of MS2CP-Pep58X causes a repression of the translation of Luc R mRNA, the slope of the corresponding straight line is about −0.6 (FIG. 7B). The applicant has shown that the system of analysis also permits the study of proteins which stimulate translation (results not shown).

TABLE 2

Preferred systems of inducible regulation

| NAME | PROMOTER | INDUCER | COMMERCIAL OR LITERATURE REFERENCE |
|---|---|---|---|
| pMSG | MMTV-LTR "(mouse mammary tumor virus)" | Dexamethasone | Amersham Pharmacia |
| pOPRSVI/MCS | RSV-LTR (<< Rous sarcoma virus >>) | IPTG | Stratagene |

TABLE 2-continued

Preferred systems of inducible regulation

| NAME | PROMOTER | INDUCER | COMMERCIAL OR LITERATURE REFERENCE |
|---|---|---|---|
| pTet-Splice | Tet | Tetracycline | Life Technologies |
| pTRE | hCMV-1 | Tetracycline or doxycycline | Clontech |
| pRev-TRE | hCMV-1 | Tetracycline or doxycycline | Clontech |
| [2]pRetro-On pRetro-Off | hCMV-1 | Tetracycline or doxycycline | Clontech |
| pIND series | ΔHSP ("Heat shock protein") | Ecdysone | Invitrogen |
| pPOP | mPGK/lacO (phosphoglycerate kinase) | IPTG | G. N. Hannan, S. A. Lehnert, E. S. MacAvoy, P. A. Jennings and P. L. Molloy, An engineered PGK promoter and lac operator-repressor system for the regulation of gene expression in mammalian cells. Gene 130 (1993), pp. 233-239. |
| pEF-LAC | hEF-1α/lacO | IPTG | Edamatsu, H., Kaziro, Y., and Itoh, H. (1997) Inducible high level expression vector for mammalian cells, pEF-LAC carrying human elongation factor 1 α promoter and lac operator. Gene 187, 289-294. |
| pBPVMT1 | mMT-I (metallothionein I) | $Cd^{++}$, $Zn^{++}$, $PMA^{++}$ | Pavlakis, G. N., and Hamer, D. H. (1983) Regulation of a metallothionein-growth hormone hybrid gene in bovine papilloma virus. Proc. Natl. Acad. Sci. USA 80, 397-401 |
| pMT | hMT-II (metallothionein II) | $Cd^{++}$, $Zn^{++}$, $PMA^{++}$ | Friedman, J. S., Cofer, C. L., Anderson, C. L., Kushner, J. A., Gray, P. P., Chapman, G. E., Stuart, M. C., Lazarus, L., Shine, J., and Kushner, P. J. (1989) High expression in mammalian cells without amplification. Bio/Technology 7, 359-362 |
| pMT302 | hMT-IIA (mutant) | $Cd^{++}$, $Zn^{++}$, $PMA^{++}$ | Makarov, S. S., Jonat, C., and Haskill, S. (1994) Hyperinducible human metallothionein promoter with a low level basal activity. Nucleic Acids Res. 22 1504-1505 |
| pIPF | hIFN-α, (interferon α) | Virus | Mori, T., Yamamoto, K., Ohta, T., Sakamoto, C., Sato, M., Koide, K., Murakami, T., Fujii, M., Fukuda, S., and Kurimoto, M. (1994) A high level and regulatable production system for recombinant glycoproteins using a human interferon-α promoter-based expression vector. Gene 144 289-293 |
| pGRE5 | 5XGRE/Ad2MLP "(glucocorticoid reponse element/adenovirus major late promoter")" | Dexamethasone | Mader, S., and White, J. H. (1993) A steroid-inducible promoter for the controlled overexpression of cloned genes in eukaryotic cells. |
| GRE5 | "high affinity glucocorticoid reponse element (GRE)/Adenovirus 2MLP" | Dexamethasone | S. Mader and J. H. White, A steroid-inducible promoter for the controlled overexpression of cloned genes in eukaryotic cells. Proc. Natl. Acad. Sci. USA 90 (1993), pp. 5603-5607 0(12) 5603-7 |
| pRDB | "DRE/MMTV (dioxin reponse element)" | TTCD' | . A. De Benedetti and R. E. Rhoads, A novel BK virus-based episomal vector for expression of foreign genes in mammalian cells. Nucleic Acids Res. 19 (1991), pp. 1925-1931. |

TABLE 3

| SEQ ID N° | Designation | Type |
|---|---|---|
| 1 | Pep58X aa | peptide |
| 2 | Pep 58H aa | peptide |
| 3 | EDEN-BP (aa84-155) | peptide |
| 4 | CUG-BP (aa155-242) | peptide |
| 5 | Fusion MS2CP-HA TAG-Pep58X | peptide |
| 6 | Fusion MS2CP-HA TAG-Pep58H | peptide |
| 7 | Fusion MS2-CP-HA TAG-Pep58X | nucleic acid |
| 8 | Fusion MS2CP-HA TAG-Pep58H | nucleic acid |
| 9 | EDENBP | peptide |
| 10 | EDENBP | nucleic acid |
| 11 | Peptide HA | peptide |
| 12 | Primer | nucleic acid |
| 13 | Primer | nucleic acid |
| 14 | Primer | nucleic acid |
| 15 | Primer | nucleic acid |
| 16 | Peptide HA | nucleic acid |

REFERENCES

AUSUBEL et T. al., (1989) Current Protocols in Molecular Biology, Green Publishing Associates and Wiley Interscience N.Y.

COLLER J. et al., 2002, Methods, vol. 26: 142-150.

EZZEDINE et al., 2002, PROC. Natl. Acad. Sci. USA, vol. 99(1): 257-262.

HOUBEN WEIL (1974); In methode der Organischen Chemie, E. Wunsh ed., volume 15-I et 15-II, Thieme, Stuttgart.

MAKRIDES, Savvas C., 1999, Protein Expr. Purif., vol. 17(2):183-202.

MERRIFIELD R B, (1965a), Nature, vol. 207 (996): 522-523

MERRIFIELD R B, (1965b), Science, vol. 150 (693):178-185.

PAILLARD L et al., 1998, The Embo Journal, vol. 17 (1) 278-287.

PAILLARD L et al., 2002, vol. 277 (5) 3232-3235.

UCHIDA N AOYUKI, Shin-ichi Hoshino, Hiroaki Imataka, Nahum Sonenberg and Toshiaki Katada.J. Biol. Chem., December 2002; 277: 50286-50292.

---

The invention claimed is:

1. A fusion protein specifically inhibiting the translation of a target polynucleotide of interest, comprising: SEQ ID NO 5.

2. A pharmaceutical composition comprising a fusion polypeptide according to claim 1.

3. A fusion protein specifically inhibiting the translation of a target polynucleotide of interest, consisting of SEQ ID NO 5.

4. A pharmaceutical composition comprising a fusion polypeptide according to claim 3.

* * * * *

SEQUENCE LISTING

<160> NUMBER OF SEQ ID NOS: 17

<210> SEQ ID NO 1
<211> LENGTH: 28
<212> TYPE: PRT
<213> ORGANISM: Xenopus laevis

<400> SEQUENCE: 1

Val Lys Phe Ala Asp Thr Gln Lys Asp Lys Glu Gln Lys Arg Met Thr
 1               5                  10                  15

Gln Gln Leu Gln Gln Gln Met Gln Gln Leu Asn Ala
            20                  25

<210> SEQ ID NO 2
<211> LENGTH: 28
<212> TYPE: PRT
<213> ORGANISM: Homo sapiens

<400> SEQUENCE: 2

Val Lys Phe Ala Asp Thr Gln Lys Asp Lys Glu Gln Lys Arg Met Ala
 1               5                  10                  15

Gln Gln Leu Gln Gln Gln Met Gln Gln Ile Ser Ala
            20                  25

<210> SEQ ID NO 3
<211> LENGTH: 84
<212> TYPE: PRT
<213> ORGANISM: Xenopus laevis

<400> SEQUENCE: 3

Phe Thr Thr Arg Ser Met Ala Gln Met Ala Ile Lys Ser Met His Gln
 1               5                  10                  15

Ala Gln Thr Met Glu Gly Cys Ser Ser Pro Ile Val Val Lys Phe Ala
            20                  25                  30

Asp Thr Gln Lys Asp Lys Glu Gln Lys Arg Met Thr Gln Gln Leu Gln
         35                  40                  45

Gln Gln Met Gln Gln Leu Asn Ala Ala Ser Met Trp Gly Asn Leu Thr
     50                  55                  60

```
Gly Leu Asn Ser Leu Ala Pro Gln Tyr Leu Ala Leu Gln Gln Thr
 65                  70                  75                  80

Ala Ser Ser Gly

<210> SEQ ID NO 4
<211> LENGTH: 88
<212> TYPE: PRT
<213> ORGANISM: Homo sapiens

<400> SEQUENCE: 4

Phe Thr Thr Arg Ala Met Ala Gln Thr Ala Ile Lys Ala Met His Gln
 1               5                  10                  15

Ala Gln Thr Met Glu Gly Cys Ser Ser Pro Met Val Val Lys Phe Ala
                20                  25                  30

Asp Thr Gln Lys Asp Lys Glu Gln Lys Arg Met Ala Gln Gln Leu Gln
            35                  40                  45

Gln Gln Met Gln Gln Ile Ser Ala Ala Ser Val Trp Gly Asn Leu Ala
        50                  55                  60

Gly Leu Asn Thr Leu Gly Pro Gln Tyr Leu Ala Leu Tyr Leu Gln Leu
 65                  70                  75                  80

Leu Gln Gln Thr Ala Ser Ser Gly
                85

<210> SEQ ID NO 5
<211> LENGTH: 189
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 5

Met Ala Tyr Pro Tyr Asp Val Pro Asp Tyr Ala Ser Val Lys Phe Ala
 1               5                  10                  15

Asp Thr Gln Lys Asp Lys Glu Gln Lys Arg Met Thr Gln Gln Leu Gln
                20                  25                  30

Gln Gln Met Gln Gln Leu Asn Ala Ala Ala Met Ala Ser Asn Phe
            35                  40                  45

Thr Gln Phe Val Leu Val Asp Asn Gly Gly Thr Gly Asp Val Thr Val
        50                  55                  60

Ala Pro Ser Asn Phe Ala Asn Gly Val Ala Glu Trp Ile Ser Ser Asn
 65                  70                  75                  80

Ser Arg Ser Gln Ala Tyr Lys Val Thr Cys Ser Val Arg Gln Ser Ser
                85                  90                  95

Ala Gln Asn Arg Lys Tyr Thr Ile Lys Val Glu Val Pro Lys Val Ala
            100                 105                 110

Thr Gln Thr Val Gly Gly Glu Glu Leu Pro Val Ala Gly Trp Arg Ser
        115                 120                 125

Tyr Leu Asn Met Glu Leu Thr Ile Pro Ile Phe Ala Thr Asn Ser Asp
 130                 135                 140

Cys Glu Leu Ile Val Lys Ala Met Gln Gly Leu Leu Lys Asp Gly Asn
145                 150                 155                 160

Pro Ile Pro Ser Ala Ile Ala Ala Asn Ser Gly Ile Tyr Gly Gly Gly
                165                 170                 175

Gly Gly Ser Gly Pro Tyr Ser Ile Val Ser Pro Lys Cys
        180                 185
```

<210> SEQ ID NO 6
<211> LENGTH: 154
<212> TYPE: PRT
<213> ORGANISM: Artificial Sequence
<220> FEATURE:
<223> OTHER INFORMATION: Description of Artificial Sequence: Synthetic
fusion protein

<400> SEQUENCE: 6

Met Ala Ser Asn Phe Thr Gln Phe Val Leu Val Asp Asn Gly Gly Thr
1               5                   10                  15

Gly Asp Val Thr Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Gln Asn Arg Lys Tyr Thr Ile Lys Val Glu
    50                  55                  60

Val Pro Lys Val Ala Thr Gln Thr Val Gly Gly Glu Glu Leu Pro Val
65                  70                  75                  80

Ala Gly Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr Gly Gly Gly Gly Ser Lys Leu Gly Ser Met Ala Tyr Pro
    130                 135                 140

Tyr Asp Val Pro Asp Tyr Ala Arg Ala Ala
145                 150

<210> SEQ ID NO 7
<211> LENGTH: 570
<212> TYPE: DNA
<213> ORGANISM: Artificial Sequence
<220> FEATURE:
<223> OTHER INFORMATION: Description of Artificial Sequence: Synthetic
fusion polynucleotide

<400> SEQUENCE: 7
atggcttacc catacgatgt tccagattac gctagcgtaa agttcgcaga cactcagaaa      60
gacaaagaac agaagcgcat gacgcagcaa cttcagcagc aaatgcagca gctcaatgca     120
gcggccgcca tggcttctaa ctttactcag ttcgttctcg tcgacaatgg cggaactggc     180
gacgtgactg tcgccccaag caacttcgct aacggggtcg ctgaatggat cagctctaac     240
tcgcgatcac aggcttacaa agtaacctgt agcgttcgtc agagctctgc gcagaatcgc     300
aaatacacca tcaaagtcga ggtgcctaaa gtggcaaccc agactgttgg tggtgaagag     360
cttcctgtag ccggatggag atcttactta aatatggaac taccattcc aattttcgcc      420
acgaattccg actgcgagct tattgttaag gcaatgcaag gtctcctaaa agatggaaac     480
ccgattccct cggccatcgc ggccaactcc ggcatctacg gaggtggagg tggatctggg     540
ccctattcta tagtgtcacc taaatgctag                                      570

<210> SEQ ID NO 8
<211> LENGTH: 570
<212> TYPE: DNA
<213> ORGANISM: Artificial Sequence
<220> FEATURE:
<223> OTHER INFORMATION: Description of Artificial Sequence: Synthetic
fusion polynucleotide

<400> SEQUENCE: 8

```
atggcttacc catacgatgt tccagattac gctagcgtaa aatttgctga tacacagaag      60
gacaaagaac agaagagaat ggcccagcag ctccagcagc agatgcagca atcagcgca     120
gcggccgcca tggcttctaa ctttactcag ttcgttctcg tcgacaatgg cggaactggc    180
gacgtgactg tcgccccaag caacttcgct aacggggtcg ctgaatggat cagctctaac    240
tcgcgatcac aggcttacaa agtaacctgt agcgttcgtc agagctctgc gcagaatcgc    300
aaatacacca tcaaagtcga ggtgcctaaa gtggcaaccc agactgttgg tggtgaagag    360
cttcctgtag ccggatggag atcttactta aatatggaac taaccattcc aattttcgcc    420
acgaattccg actgcgagct tattgttaag gcaatgcaag gtctcctaaa agatggaaac    480
ccgattcccct cggccatcgc ggccaactcc ggcatctacg aggtggagg tggatctggg    540
ccctattcta tagtgtcacc taaatgctag                                     570
```

<210> SEQ ID NO 9
<211> LENGTH: 489
<212> TYPE: PRT
<213> ORGANISM: Xenopus laevis

<400> SEQUENCE: 9

```
Met Asn Gly Thr Met Asp His Pro Asp His Pro Asp Pro Asp Ser Ile
  1               5                  10                  15

Lys Met Phe Val Gly Gln Val Pro Arg Ser Trp Ser Glu Lys Glu Leu
             20                  25                  30

Arg Glu Leu Phe Glu Gln Tyr Gly Ala Val Tyr Glu Ile Asn Val Leu
         35                  40                  45

Arg Asp Arg Ser Gln Asn Pro Pro Gln Ser Lys Gly Cys Cys Phe Ile
     50                  55                  60

Thr Phe Tyr Thr Arg Lys Ala Ala Leu Glu Ala Gln Asn Ala Leu His
 65                  70                  75                  80

Asn Met Lys Val Leu Pro Gly Met His His Pro Ile Gln Met Lys Pro
                 85                  90                  95

Ala Asp Ser Glu Lys Asn Asn Ala Val Glu Asp Arg Lys Leu Phe Ile
            100                 105                 110

Gly Met Val Ser Lys Asn Cys Asn Glu Asn Asp Ile Arg Ala Met Phe
        115                 120                 125

Ser Pro Phe Gly Gln Ile Glu Glu Cys Arg Ile Leu Arg Gly Pro Asp
    130                 135                 140

Gly Met Ser Arg Gly Cys Ala Phe Val Thr Phe Thr Thr Arg Ser Met
145                 150                 155                 160

Ala Gln Met Ala Ile Lys Ser Met His Gln Ala Gln Thr Met Glu Gly
                165                 170                 175

Cys Ser Ser Pro Ile Val Val Lys Phe Ala Asp Thr Gln Lys Asp Lys
            180                 185                 190

Glu Gln Lys Arg Met Thr Gln Gln Leu Gln Gln Gln Met Gln Gln Leu
        195                 200                 205

Asn Ala Ala Ser Met Trp Gly Asn Leu Thr Gly Leu Asn Ser Leu Ala
    210                 215                 220

Pro Gln Tyr Leu Ala Leu Leu Gln Gln Thr Ala Ser Ser Gly Asn Leu
225                 230                 235                 240

Asn Ser Leu Ser Gly Leu His Pro Met Gly Ala Glu Tyr Gly Thr Gly
                245                 250                 255
```

-continued

Met Thr Ser Gly Leu Asn Ala Ile Gln Leu Gln Asn Leu Ala Ala Leu
            260                 265                 270

Ala Ala Ala Ala Ser Ala Ala Gln Asn Thr Pro Ser Ala Gly Ala Ala
        275                 280                 285

Leu Thr Ser Ser Ser Ser Pro Leu Ser Ile Leu Thr Ser Ser Gly Ser
    290                 295                 300

Ser Pro Ser Ser Asn Asn Ser Ser Ile Asn Thr Met Ala Ser Leu Gly
305                 310                 315                 320

Ala Leu Gln Thr Leu Ala Gly Ala Thr Ala Gly Leu Asn Val Asn Ser
                325                 330                 335

Leu Ala Gly Met Ala Ala Phe Asn Gly Gly Leu Gly Ser Ser Leu Ser
            340                 345                 350

Asn Gly Thr Gly Ser Thr Met Glu Ala Leu Ser Gln Ala Tyr Ser Gly
        355                 360                 365

Ile Gln Gln Tyr Ala Ala Ala Ala Leu Pro Ser Leu Tyr Asn Gln Ser
    370                 375                 380

Leu Leu Ser Gln Gln Gly Leu Gly Ala Ala Gly Ser Gln Lys Glu Gly
385                 390                 395                 400

Pro Glu Gly Ala Asn Leu Phe Ile Tyr His Leu Pro Gln Glu Phe Gly
                405                 410                 415

Asp Gln Asp Leu Leu Gln Met Phe Met Pro Phe Gly Asn Val Val Ser
            420                 425                 430

Ser Lys Val Phe Ile Asp Lys Gln Thr Asn Leu Ser Lys Cys Phe Gly
        435                 440                 445

Phe Val Ser Tyr Asp Asn Pro Val Ser Ala Gln Ala Ala Ile Gln Ser
    450                 455                 460

Met Asn Gly Phe Gln Ile Gly Met Lys Arg Leu Lys Val Gln Leu Lys
465                 470                 475                 480

Arg Ser Lys Asn Asp Ser Lys Pro Tyr
                485

<210> SEQ ID NO 10
<211> LENGTH: 1470
<212> TYPE: DNA
<213> ORGANISM: Xenopus laevis

<400> SEQUENCE: 10
atgaatggca caatggacca cccagaccat ccggatccgg actccatcaa gatgtttgtg     60
ggtcaggttc ctcgaagctg gtcagagaaa gagctaagag aactcttcga gcagtacgga    120
gccgtctatg aaattaatgt tctccgagac agaagccaga atcctcctca gagcaaagga    180
tgctgtttta ttactttcta cacaagaaaa gctgcgttag aagcacagaa tgctttgcac    240
aacatgaaag ttctccctgg gatgcatcat ccaatacaga tgaagccagc cgacagtgaa    300
aagaataatg ctgtggaaga accgaaagcta tttatcggaa tggtttccaa gaattgtaat    360
gagaatgata tccgggccat gttctctccg tttggacaga tagaggaatg tcgtatcctg    420
cgaggccctg atggaatgag cagaggatgt gcattcgtta cgtttacaac tagatccatg    480
gcacagatgg caatcaaatc catgcaccaa gcacaaacca tggagggctg ttcctcacca    540
atagtggtaa agttcgcaga cactcagaaa gacaaagaac agaagcgcat gacgcagcaa    600
cttcagcagc aaatgcagca gctcaatgca gcctcaatgt ggggtaaccc gactggactg    660
aacagcttgg cacccagta tttagcactc ctcagcagaa ccgcctcctc tgggaacctc    720
aactccctaa gtggtctcca ccctatggga gctgagtacg gcactggaat gacatcaggg    780

```
cttaatgcca tacagttaca gaatttggca gctttagcgg ctgctgctag tgctgcgcag      840
aacaccccaa gtgcaggagc agcgctcact tcttccagca gcccctcag catcctaacc       900 agttccggtt cctcccccag ttcaaataac tcatccatca acaccatggc atccctagga      960
gctctacaga cattggctgg ggccacagct ggtctcaatg tcaattcgct tgcaggtatg     1020
gctgcgttta atggaggcct aggcagcagt ctctccaatg gcactggcag tacgatggaa     1080
gcccttagtc aagcttactc tgggattcag cagtatgctg ccgctgcact tccttcactc     1140
tataaccaga gccttttgtc acaacagggt ttggggctg cggggagtca gaaagaaggc      1200
ccagaaggag ccaaccttt tatataccac ctacccagg agtttgggga ccaggatctc       1260
ctgcagatgt tcatgccatt tggaaatgtt gtgtcctcca agttttcat cgacaaacaa      1320 acgaacctca gcaaatgttt tggcttcgta agttacgaca tcccgtttc tgctcaggct      1380 gctatccagt ccatgaacgg ctttcagatc ggaatgaaac gcctgaaagt ccaactcaaa    1440
cgctccaaga atgacagcaa accctactga                                      1470
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Pro Tyr Asp Val Pro Asp Tyr Ala
 1               5

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atgctagcgt aaagttcgca gacactcaga aag                                    33

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgcggccgc tgcattgagc tgctgcattt gc                                     32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atgctagcgt aaaatttgct gatacacaga ag                                     32

<210> SEQ ID NO 15

```
-continued
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atgcggccgc tgcgctgatt tgctgcatct gc                                    32

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tacccatacg atgttccaga ttacgct                                          27

<210> SEQ ID NO 17
<211> LENGTH: 10
<212> TYPE: RNA
<213> ORGANISM: Artificial Sequence
<220> FEATURE:
<223> OTHER INFORMATION: Description of Artificial Sequence: Synthetic
      poly-A tail

<400> SEQUENCE: 17
aaaaaaaaaa                                                             10
```